United States Patent
Maccecchini

(10) Patent No.: US 12,390,448 B2
(45) Date of Patent: *Aug. 19, 2025

(54) PREVENTION OR OF DISEASE STATES DUE TO METAL DIS-HOMEOSTASIS VIA ADMINISTRATION OF POSIPHEN TO HEALTHY OR SICK HUMANS

(71) Applicant: ANNOVIS BIO, INC., Berwyn, PA (US)

(72) Inventor: Maria Maccecchini, West Chester, PA (US)

(73) Assignee: ANNOVIS BIO, INC., Berwyn, PA (US)

( * ) Notice: Subject to any disclaimer, the term of this patent is extended or adjusted under 35 U.S.C. 154(b) by 196 days.

This patent is subject to a terminal disclaimer.

(21) Appl. No.: 18/178,941

(22) Filed: Mar. 6, 2023

(65) Prior Publication Data

US 2023/0355585 A1 Nov. 9, 2023

Related U.S. Application Data

(63) Continuation of application No. 16/827,194, filed on Mar. 23, 2020, now Pat. No. 11,596,621, which is a continuation of application No. 15/987,420, filed on May 23, 2018, now abandoned.

(60) Provisional application No. 62/510,554, filed on May 24, 2017.

(51) Int. Cl.
  *A61K 31/407* (2006.01)
  *A61K 9/00* (2006.01)
  *A61P 3/00* (2006.01)

(52) U.S. Cl.
  CPC .......... *A61K 31/407* (2013.01); *A61K 9/0053* (2013.01); *A61P 3/00* (2018.01)

(58) Field of Classification Search
  CPC .................................................. A61K 31/407
  See application file for complete search history.

(56) References Cited

U.S. PATENT DOCUMENTS

| | | | |
|---|---|---|---|
| 5,171,750 A | 12/1992 | Brossi et al. | |
| 5,409,948 A | 4/1995 | Greig et al. | |
| 6,410,747 B1 | 6/2002 | Greig et al. | |
| 6,495,700 B1 | 12/2002 | Bruening et al. | |
| 6,683,105 B2 | 1/2004 | Greig et al. | |
| 7,153,882 B2 | 12/2006 | Greig et al. | |
| 7,625,942 B2 | 12/2009 | Bruinsma et al. | |
| 7,786,162 B2 | 8/2010 | Greig et al. | |
| 7,994,210 B2 | 8/2011 | Bruinsma et al. | |
| 8,258,172 B2 | 9/2012 | Greig et al. | |
| 8,691,864 B2 | 4/2014 | Greig et al. | |
| 11,596,621 B2 * | 3/2023 | Maccecchini | A61K 31/407 |
| 2002/0094999 A1 | 7/2002 | Greig et al. | |
| 2004/0024043 A1 | 2/2004 | Greig et al. | |
| 2005/0013869 A1 | 1/2005 | Chaw et al. | |
| 2005/0182044 A1 | 8/2005 | Bruinsma | |
| 2005/0272804 A1 | 12/2005 | Bruinsma | |
| 2007/0037848 A1 | 2/2007 | Masters et al. | |
| 2010/0298389 A1 | 11/2010 | Elmaleh et al. | |
| 2011/0021594 A1 | 1/2011 | Greig et al. | |
| 2012/0225922 A1 | 9/2012 | Maccecchini | |

FOREIGN PATENT DOCUMENTS

| | | |
|---|---|---|
| WO | WO0166114 | 9/2001 |
| WO | WO0248150 | 6/2002 |
| WO | WO03082270 | 10/2003 |
| WO | WO2004034963 | 4/2004 |
| WO | WO2005089746 | 9/2005 |
| WO | WO2005123068 | 12/2005 |

(Continued)

OTHER PUBLICATIONS

Cullen et al. "Brain Beta-Amyloid 42 in Mice Treated Orally with Posiphen Tartrate is Significantly Lower than in Vehicle Controls," 9th International Geneva/Springfield Symposium on Advances in Alzheimer Therapy; (Apr. 19, 2006)

Holloway et al. "Mechanism of Action of Posiphen in CSF of mildly Cognitive Impaired Patients," QR Pharma, Inc., Radnor, PA.

Soares et al., "Aβ Variability and Effects of Gamma Secretase Inhibition on Plasma and Cerebrospinal Fluid Levels of Aβ Peptide in Healthy Volunteers" Pfizer Global Research and Development, New London, CT.

Marutle et al. "Modulation of human neural stem cell differentiation in Alzheimer (APP23) transgenic mice by phenserine" The National Academy of Sciences of the USA; vol. 104, No. 30, pp. 12506-12511, (Jul. 24, 2007). .

(Continued)

*Primary Examiner* — Rei Tsang Shiao
(74) *Attorney, Agent, or Firm* — DAVIDSON KAPPEL LLC

(57) ABSTRACT

The invention relates in part to a method of maintaining heavy metal homeostasis in healthy humans, comprising chronically administering to healthy humans a pharmaceutical composition consisting of from about 1 mg to less than about 200 mg of Posiphen or a pharmaceutically acceptable salt thereof together with one or more pharmaceutically acceptable excipients, on a once a day basis. By virtue of this method, prophylactic treatment of a potential disease state such as a neurodegenerative disease, cardiovascular homeostasis, cancer, vital organ homeostasis, and the like. The invention also relates in part to a method of restoring heavy metal homeostasis in sick patients, comprising chronically administering to a sick patient a pharmaceutical composition consisting of from about 1 mg to less than about 200 mg of Posiphen or a pharmaceutically acceptable salt thereof together with one or more pharmaceutically acceptable excipients, on a once a day basis. By virtue of this method, treatment of a potential disease state such as a neurodegenerative disease, cardiovascular disease, cancer, vital organ dysfunction and heavy metal dis-homeostasis, and the like.

20 Claims, 15 Drawing Sheets

Specification includes a Sequence Listing.

(56) References Cited

FOREIGN PATENT DOCUMENTS

| WO | WO2010117727 | 10/2010 |
|---|---|---|
| WO | WO2012154285 | 11/2012 |
| WO | WO 2014/179303 A1 | 11/2014 |
| WO | WO2017030968 | 2/2017 |

OTHER PUBLICATIONS

Brazzolotto et al., "Structural Changes Associated with Switching Activities of Human Iron Regulatory Protein 1*" The Journal of Biological Chemistry; vol. 277, No. 14, pp. 11995-12000, (2002).

Shaw et al., "Phenserine regulates translation of β-amyloid precursor protein mRNA by a putative interleukin-1 responsive element, a target for drug development" PNAS, vol. 98, No. 13; pp; 7605-7610, (Jun. 19, 2001).

Lahiri et al. "The Experimental Alzheimer's Disease Drug Posiphen [(+)-Phenserine] Lowers Amyloid-β Peptide Levels in Cell Culture and Mice" The Journal of Pharmacology and Experimental Therapeutics, vol. 320, No. 1; pp; 386-396; (2007).

Selkoe, "Defining Molecular Targets to Prevent Alzheimer Disease" American Medical Association; pp. 192-195; (2005).

Kadir et al. "Effect of Phenserine Treatment on Brain Functional Activity and Amyloid in Alzheimer's Disease" American Neurological Association, Wiley-Liss, Inc.; pp. 621-631; (2008).

Khachaturian, "Diagnosis of Alzheimer's Disease" Arch Neurology; vol. 42, pp. 1097; (Nov. 1985).

Cahill et al. "Amyloid Precursor Protein and Alpha Synuclein Translation, Implications for Iron and Inflammation in Neurodegenerative diseases" Biochim Biophys Acta. 1790(7): 615-628 (Jul. 2009).

Maccecchini et al. " Posiphen as a candidate drug to lower CSF amyloid precursor protein, amyloid-β peptide and levels: target engagement, tolerability and pharmacokinetics in humans" J Neurol Neurosurg Psychiatry; vol. 83; pp. 894-902; (2012).

Duce et al. "Iron-Export Ferroxidase Activity of β-Amyloid Precursor Protein Is Inhibited by Zinc in Alzheimer's Disease" Cell; pp. 1-10; (2010), doi: 10.1016/j.cell.2010.08.014.

Kounnas et al. "Modulation of ϒ-Secretase Reduces β-Amyloid Deposition in a Transgenic Mouse Model of Alzheimer's Disease" Neuron; pp. 1-12; (2010).

Mikkilineni et al. "The Anticholinesterase Phenserine and Its Enantiomer Posiphen as 5' Untranslated-Region-Directed Translation Blockers of the Parkinson's Alpha Synuclein Expression" Hindawi Publishing Corporation; vol. 2012, Article ID 142372.

Venti et al. "The Integrated Role of Desferrioxamine and Phenserine Targeted to an Iron-Responsive Element in the APP-mRNA 5'-Untranslated Region" Ann. N.Y. Acad. Sci. Vol 1035: pp. 34-58 (2004).

Bandyopadhyay et al. "Novel 5' Untranslated Region Directed Blockers of Iron-Regulatory Protein-1 Dependent Amyloid Precursor Protein Translation: Implications for Down Syndrome and Alzheimer's Disease" PLOS One; vol. 8, Issue 7; pp. 1-14 (2013).

Maccecchini, "Targeting Alzheimer's with Novel Therapeutics" QR Pharma, Inc. Neuroscience Network; presented by Maria Maccecchini on May 11, 2010.

Harold W Holloway et al: "Posiphen and Analogs: Experimental Alzheimer' Agents that Reduce Amyloid-[beta] Peptide by Lowering Amyloid Precursor Protein Levels in Culture and In Vivo" , 42nd Annual Winter Conference on Brain Research , Jan. 25, 2009 (Jan. 25, 2009) , 42nd Annual Winter Conference on Brain Research. Abstract only.

Maccecchini et al: "Targeting Alzheimer's with Novel Therapeutics", May 11, 2010 (May 11, 2010), Neuroscience Network, << http:l/www.qrpharma.comlpdf/2010-5-11 Alzheimers Research Today Maria Maccecchini slides.pdf>>. Last accessed Jul. 22, 2014.

Maria L. Maccecchini: "Mechanism of Action of Posiphen : From Model to Human" , Jan. 26, 2011 (Jan. 26, 2011) , 44nd Annual Winter Conference on Brain Research, << http://wwwqrpharma. com/pdfIWCBR Talk Jan 2011.pdf>>. Last accessed Jul. 22, 2014.

Kadir et al: "Long-term effect of phenserine treatment in Alzheimer patients as assessed by PET and CSF biomarkers", Alzheimer's & Dementia the Journal of the Alzheimer's Association vol. 5, No. 4; p. 6.

Melo et al. Annals of the NY Academy of Sci., 1096, 1, 2007.

Maccecchini et al. (Poster presentations, Alzheimer's and Dementia, Jul. 2009, 5, 4, S1, p. 247-248).

Lahiri et al. (The J of Pharmacology and Experimental Therapeutics, 320, 1, 386-396, 2007).

Tomiyama, (The J of Biol. Chem, 271, 12, 6839-44, 1996).

Galvan, et al., "Reversal of Alzheimer's-like pathology and behavior in human APP transgenic mice by mutation of Asp664," PNAS, May 2, 2006, I03(18): pp. 7130-7135.

Nikolaev, et al., "APP binds DR6 to trigger axon pruning and neuron death via distinct caspases," Nature, Feb. 19, 2009, 457(19): pp. 981-990.

Takeda, et al., "Mechanisms of Neuronal Death in Synucleinopathy," Journal of Biomedicine and Biotechnology, 2006, vol. 2006, Article ID 19365, pp. 1-4.

Rogers, et al., "The alpha-synuclein 5 'untranslated region targeted translation blockers: anti-alpha synuclein efficacy of cardiac glycosides and Posiphen," .1. Neural Transm, Oct. 15, 2010, DOI 10.1007/s00702-010-0513-5.

Cho, et al., "Selective Translational Control of the Alzheimer Amyloid Precursor Protein Transcript by Iron Regulatory Protein-1," Journal of Biological Chemistry, Oct. 8, 2010, 285(41): pp. 31217-31232.

Khachaturian, "Diagnosis of Alzheimer's Disease," Arch Neural, Nov. 1985, 42: pp. 1097-1105.

International Search Report from International WIPO Publication No. WO 2012/154285 dated Aug. 17, 2012.

Maccecchini et al. "Posiphen lowers amyloid precursor protein and amyloid beta as well as acetylcholinesterase levels in culture, animals and humans" International Conference on Alzheimer's Disease; Jul. 12, 2009 (Abstract is retrieved from http://www.qrpharma.com/pdf/ICAD_Posiphen_06-30-2009.pdf on May 19, 2012; Publication date is retrieved from http://www/grpharma.com/pdf/WCBR_Posiphen_01%206%2009-20Poster.pdf on May 19, 2012) abstract, Figs. 1, 3, 4, 8(2).

Greig et al. "The experimental Alzheimer drug phenserine: preclinical pharmacokinetics and pharmacodynamics" Acta Neurol Scand 2000: Supplement 176: pp. 74-84.

Office Action from corresponding Korean Patent Application No. 10-2013-7025992 dated Jul. 30, 2018.

Janas et al. "The cholinesterase inhibitor, phenserine, improves Morris water maze performance of scopolamine-treated rats" Life Sciences, Pergamon Press, Oxford, GB, vol. 76, No. 10, (Jan. 21, 2005) pp. 1073-1081.

Pike et al. "Effect of tetrahydroaminoacridine, a cholinesterase inhibitor, on cognitive performance following experimental brain injury" Journal of Neurotrauma, vol. 14, No. 12, (Dec. 1997) pp. 897-905.

David et al. "Cognitive impairments Induced by Concussive Mild Traumatic Brain Injury in Mouse Are Ameliorated by Treatment with Phenserine via Multiple Non-Cholinergic and Cholinergic Mechanisms" POLS One, vol. 11, No. 6, (Jun. 2, 2016) pp. e0156493.

International Search Report from International PCT Application No. PCT/US2016/046794 dated Feb. 23, 2017.

Hentze et al., "Two to Tango: Regulation of Mammalian Iron Metabolism" Cell. Jul. 9, 2010, vol. 142, No. 1, pp. 42-38; abstract; p. 26, $2^{nd}$ col. $4^{th}$ paragraph.

International Search Report from International PCT Application No. PCT/US18/34130 dated Sep. 4, 2018.

International Written Opinion from International PCT Application No. PCT/US2018/034130 dated Nov. 26, 2019.

U.S Department of Health and Human Services Food and Drug Administration Center for Drug Evaluation and Research (CDER) "Guidance for Industry Estimating the Maximum Safe Starting Dose in Initial Clinical Trials for Therapeutics in Adult Healthy Volunteers"; Jul. 6, 2005.

Maccecchini et al. "Posiphen: Experimental Alzheimer Agent that Lowers Amyloid Precursor Protein Levels in Culture and In Vivo";

(56) References Cited

OTHER PUBLICATIONS

Dept. Psychiatry, Institute Psychiatric Research, Indiana Univ., Indianapolis, IN: Department of Neuroscience, Center of Aging, Medical University of S. Carolina, Charleston, SC;. PowerPoint Presentation. Dated Jan. 2011.
Summons to Attend Oral Proceedings mailed on Apr. 25, 2019 in connection to European Patent Application No. 12 782 326.8.
Larson et al. (Annu. Rev. Publ. Health 13L431-49) (Year: 1992).
CAS Registry (1998, p. 1) (Year: 1998).
Phukan et al. (http://neurology.thelancet.com, vol. 6, Nov. 2007). (Year: 2007).
Klein (Phenserine, Expert Opin Investig. Drugs 2007, 16(7): 1087-1097 (Year: 2007).
Enright (https://louisaenright.com/2011 /11 /), 2011 (Year: 2011).
Novak et al. (Huntington's Disease, BMJ, Jul. 3, 2010). (Year: 2010).
European Search Report from corresponding application EP 18 80 5102 dated May 12, 2021.
Bush J. of Alzheimer's Dis, 2013, 33 Suppl 1: S277-81.

* cited by examiner

A) b-APP           D) b-APP + IRP1 + Posiphen + iron
B) b-APP + IRP1        E) b-APP + IRP1 + iron
C) b-APP + IRP1 + Posiphen      F) APP + IRP1 + Posiphen + iron

Figure 16

| Decrease in αSYN in Gut of tg PAC A53T Treated with Posiphen | | | |
|---|---|---|---|
| Preliminary Data | | | |
| Treatment Time in Weeks | 3 | 10 | 21 |
| % Decrease Compared to Control | 9.6 | 29.4 | 37.9 |
| Statistical Significance p | 0.4857 | 0.0342 | 0.0286 |
| Posiphen dose in mg/kg | 0  10 | 0  10 | 0  10 |
| Sample Western Blot | ▬ ▬ | ▬ ▬ | ▬ ▬ |

Figure 17

| Neurotoxic aggregating proteins | Brain levels in Posiphen-treated mice as % of controls | p-Value |
|---|---|---|
| APP | 60.2 | 0.0080 |
| CTF-A | 61.1 | 0.0311 |
| CTF-B | 53.2 | 0.0024 |
| Aβ42 | 35.5 | 0.0008 |
| Tau | 49.1 | 0.0302 |

Figure 18 a
Figure 18b
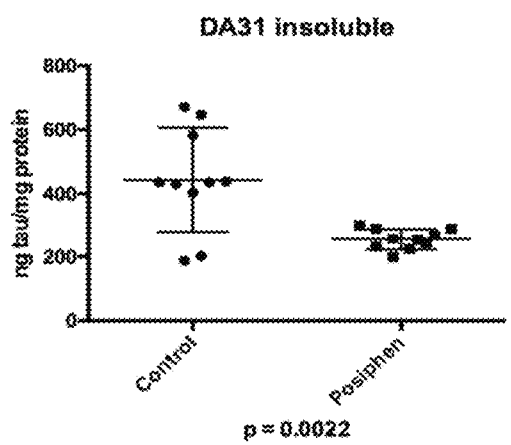
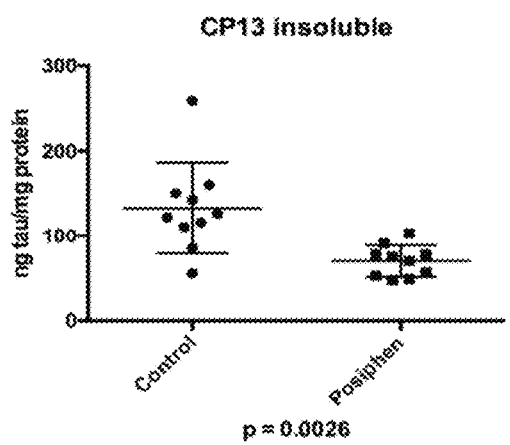
Figure 18c
Figure 18d
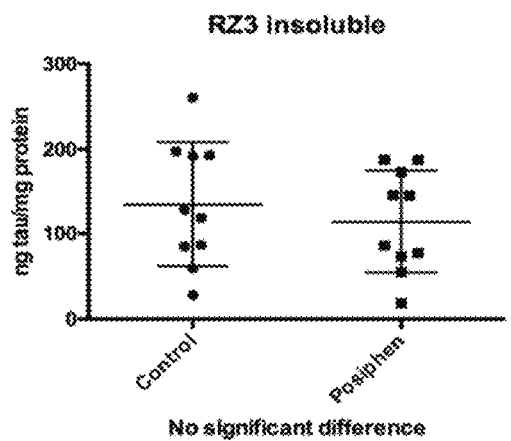
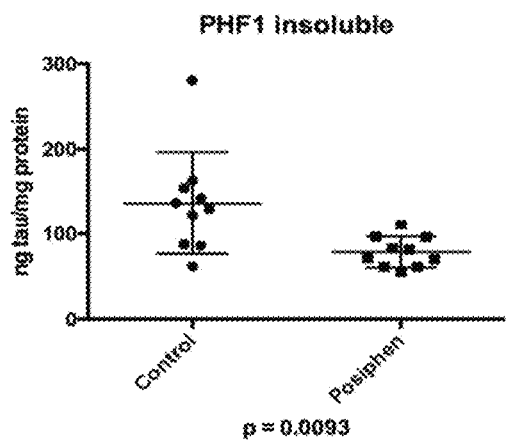

SEQUENCE LISTING

```
Sequence total quantity: 4
SEQ ID NO: 1             moltype = RNA   length = 37
FEATURE                  Location/Qualifiers
misc_feature             1..37
                         note = H-Ferritin protein
source                   1..37
                         mol_type = other RNA
                         organism = synthetic construct
SEQUENCE: 1
gggtttcctg cttcaacagt gcttggacgg aacccgg                              37

SEQ ID NO: 2             moltype = RNA   length = 37
FEATURE                  Location/Qualifiers
misc_feature             1..37
                         note = APP protein
source                   1..37
                         mol_type = other RNA
                         organism = synthetic construct
SEQUENCE: 2
gcggtggcgg cgcgggcaga gcaaggacgc ggcggat                              37

SEQ ID NO: 3             moltype = RNA   length = 35
FEATURE                  Location/Qualifiers
misc_feature             1..35
                         note = H-Ferritin protein
source                   1..35
                         mol_type = other RNA
                         organism = synthetic construct
SEQUENCE: 3
ggggtttcct gcttcaacag tgcttggacg gaacc                                35

SEQ ID NO: 4             moltype = RNA   length = 35
FEATURE                  Location/Qualifiers
misc_feature             1..35
                         note = APP Protein
```

```
source          1..35
                mol_type = other RNA
                organism = synthetic construct
SEQUENCE: 4
ggtggcggcg cgggcagagc aaggacgcgg cggat                                    35
```

PREVENTION OR OF DISEASE STATES DUE TO METAL DIS-HOMEOSTASIS VIA ADMINISTRATION OF POSIPHEN TO HEALTHY OR SICK HUMANS

FIELD OF THE INVENTION

The present patent application concerns a method of maintaining or restoring metal homeostasis in healthy humans or sick patients as well as methods of preventing disease states and restoring health via administration of Posiphen.

SEQUENCE LISTING

The present patent application sets forth the informational requirements for the content of a "Sequence Listing" part of the specification that must be submitted in accordance with 37 CFR § 1.821(c) as part of the application.

BACKGROUND OF THE INVENTION

Neurodegenerative diseases generally affect abstract thinking, skilled movements, emotional feelings, cognition, memory and other abilities. Despite differences in clinical symptoms and disease progression, disorders from this group share key common features: most of them have both sporadic and inherited origins, all of them appear later in life, and their pathology is characterized by neuronal loss and synaptic abnormalities. Until recently, no common molecular mechanism had been identified among these diseases. However, various neurodegenerative diseases, such as Alzheimer's disease (AD), Parkinson's disease (PD), Huntington's disease (HD), transmissible spongiform encephalopathies (TSEs), and amyotrophic lateral sclerosis (ALS), have been shown to share a common cause and pathological mechanism the overexpression, misfolding, aggregation and accumulation of proteins in the brain, resulting in neuronal apoptosis. The hallmark feature of conformational disorders is that a particular protein folds into a stable alternative conformation, which in most cases results in its aggregation and accumulation in tissues as fibrillar deposits. These deposits have similar morphological, structural and staining characteristics. Multidisciplinary studies strongly support this shared cause and pathological mechanism, suggesting that there may be a common therapy for these devastating disorders.

Mutations in the genes that encode the protein components of fibrillar aggregates are genetically associated with the inherited forms of all neurodegenerative diseases. The familial forms usually have an earlier onset and greater severity than sporadic cases and are also associated with a greater amount of protein aggregates (Soto, 2003, Nature Rev. 4:49).

Neurotoxic aggregating proteins have not only a common aggregating pathway, but also common regulatory pathways for their transcription and translation. While their transcription is activated by copper and/or zinc ions (Bush et al., 2003, Proc. Natl. Acad. Sci. U.S.A. 100(20):11193-94), their translation is upregulated by iron and down-regulated by iron regulatory protein 1 (IRP1). Specifically, their mRNAs are regulated via the 5'-untranslated region (5'UTR) of their transcript, which folds into a unique RNA stem loop with a CAGUGN apical loop similar to that encoded in the canonical iron-responsive element (IRE) of L- & H-ferritin mRNAs. IRP1 binds to this IRE stem look and inhibits the translation of the mRNA by the ribosome (Cho et al., 2010, J. Biol. Chem. 285(41):31217).

Examples of neurotoxic aggregating proteins are Aβ (amyloid-β peptide, a fragment of APP), Tau, alpha-synuclein (aSYN), transmissible spongiform encephalopathy (TSE) prions SOD (super oxide dismutase) proteins, huntingtin (HTT), TDP43 and c9orf72.

APP/Abeta

Alzheimer's disease (AD) is the most common progressive dementia associated with aging. The cholinergic system is the earliest and most profoundly affected neurotransmitter system in AD, with substantial losses in the forebrain, cortex and hippocampus, which are critical in the acquisition, processing and storage of memories (Terry et al., 1991, Ann. Neurol. 30:572-80; Giacobini, In "Alzheimer's Disease: Molecular Biology to Therapy"; Becker & Giacobini, Eds.; Birkhauser: Boston, 1997; pp 188-204; Becker et al., In "Alzheimer's Disease: from Molecular Biology to Therapy"; Becker & Giacobini, Eds.; Birkhauser: Boston, 1997; pp 257-66).

The major neuropathological hallmarks of AD are β-amyloid plaques, neurofibrillary tangles, and synaptic loss. In particular, amyloid-β precursor protein (APP) is cleaved into a number of toxic peptides, one of them being amyloid-β (Aβ): a hydrophobic, neurotoxic self-aggregating 40 to 42 amino-acid peptide that accumulates preferentially within senile plaques in the brain. Other peptides are also cleaved from the N-terminus and C terminus end of APPs. These peptides attack multiple pathways of neuronal cell life, leading to synaptic loss and nerve cell death. This sequence of events induces neuroinflammation and leads to cognitive impairment and neurodegeneration.

In an original hypothesis for AD treatment, inhibition of the accumulation of Aβ in the brain could positively affect the course of AD. Recently, this hypothesis has been expanded by recognizing that APP in the absence of trophic factors is shed from the surface of neuronal cells and processed into an amino terminal fragment (N-APP). This fragment binds to DR6 receptors and induces nerve cell death (Nicolaev et al., 2009, Nature 457:981-90). Furthermore, C31 (another factor cleaved from the C-terminus end of APP) has been found to cause nerve cell degeneration and death in tissue culture cells and in transgenic mice (Galvan et al., 2006, PNAS 103(18):7130-35). Overexpression of C31 has been also shown to lead to neuronal degeneration without Aβ toxicity and plaque deposition. In all three cases (cell death triggered by N-APP, Aβ and/or C31 accumulation), reducing APP synthesis could be beneficial to the preservation of brain cells, by reducing the formation of neurotoxic plaque through the Aβ pathway and by inhibiting the formation of nerve cell-killing toxic N-terminus and C-terminus fragments.

Tau

Even though tau is not a member of the iron regulated neurotoxic protein family, it is overexpressed and aggregates in a number of tauopathies. Conditions in which neurofibrillary tangles are commonly observed include: Alzheimer's disease, progressive supranuclear palsy, dementia pugilistica, chronic traumatic encephalopathy, frontotemporal dementia and parkinsonism linked to chromosome 17, Lytico-Bodig disease (Parkinson-dementia complex of Guam), Tangle-predominant dementia, with NFTs similar to AD, but without plaques. Tau deposits tend to appear in the very old, Picks disease and a number of other neuropathies. Tau's fibrillary tangles are found in most neurodegenerative disorders.

DS, APP/Abeta/SOD1

Down syndrome (DS) results when abnormal cell division involving chromosome 21 results in extra genetic material. It is most often caused by a genetic variation known as trisomy 21, wherein there are three copies of chromosome 21 instead of the usual two copies in all cells. Chromosome 21 contains the genes for APP and SOD1. Overexpression of these genes is responsible for the characteristic features and developmental problems of DS, such as physical growth delays, characteristic facial features and mild to moderate intellectual disability.

aSYN

In humans, alpha-synuclein is encoded by the SNCA gene. An alpha-synuclein fragment, known as the non-Aβ component (NAC) of Alzheimer's disease originally found in an amyloid-enriched fraction is shown to be a fragment of its precursor protein, NACP (now referred to as human alpha-synuclein).

PD, aSYN

Parkinson's disease (PD) is a chronic and progressive movement disorder that involves the malfunction and death of neurons in the substantia nigra region of the brain. Some of these dying neurons produce dopamine, a chemical that sends messages to the part of the brain that controls movement and coordination. As PD progresses, dopamine is depleted from the basal ganglia, which results in major disruptions in the connections to the thalamus and motor cortex and leads to parkinsonian signs such as bradykinesia. It has been found that a hallmark of Parkinson's disease—clumps of alpha-synuclein, called Lewy Bodies—are found not only in the mid-brain but also in the brain stem, the gut and the olfactory bulb. Lewy bodies and aSYN aggregates are present in multiple nerves from the periphery to the brain and, while motor symptoms are associated with Lewy bodies in the brain, non-motor symptoms are associated with aggregates in the periphery. In fact, the intestines have dopamine cells that degenerate in Parkinson's, they accumulate aSYN aggregates, which are responsible for the gastrointestinal symptoms that are part of the disease. Non-motor symptoms in general are experienced by all people with PD before any motor sign of the disease appears. Lewy bodies are also found in several other brain disorders, including dementia with Lewy bodies (DLB). Evidence suggests that dementia with Lewy bodies, Parkinson's disease and Parkinson's disease dementia may be linked to the same underlying abnormalities in brain processing of alpha-synuclein. Many of those afflicted with both dementia with Lewy bodies and Parkinson's disease dementia also have plaques and tangles—which are the hallmark of Alzheimer's disease. Thus, there is an inter-relationship between the Parkinson's disease-related protein alpha-synuclein and the Alzheimer's Aβ-amyloid plaque protein.

TSEs

Transmissible spongiform encephalopathies (TSEs, collectively known as prion diseases) are a group of progressive conditions that affect the brain and nervous system of mammals, and include devastating diseases as bovine spongiform encephalopathy (BSE, also known as "mad cow disease") in cattle, and classic Creutzfeldt-Jakob disease, new variant Creutzfeldt-Jakob disease (nvCJD, a human disorder related to mad cow disease), Gerstmann-Sträussler-Scheinker syndrome, fatal familial insomnia and kuru (CJD) in humans. Mental and physical abilities deteriorate in the afflicted patients, and myriad tiny holes appear in the cortex, causing it to appear like a sponge (hence 'spongiform') when brain tissue obtained at autopsy is examined under a microscope. The disorders cause impairment of brain function, including memory changes, personality changes and problems with movement that worsen over time.

Unlike other kinds of infectious diseases caused by microbes or viruses, the infectious agent in TSEs is a specific protein called prion protein. Misshaped prion proteins carry the disease between individuals and cause deterioration of the brain. TSEs are unique diseases, in that their etiology may be genetic, sporadic or infectious via ingestion of infected foodstuffs and via iatrogenic means (e.g. blood transfusion). Most TSEs are sporadic and occur in an animal with no prion protein mutation. Inherited TSE occurs in animals carrying a rare mutant prion allele, which expresses prion proteins that contort by themselves into the disease-causing conformation.

The degenerative tissue damage caused by human prion diseases (Creutzfeldt-Jakob disease, Gerstmann-Sträussler-Scheinker syndrome, and kuru) is characterised by four features: spongiform change, neuronal loss, astrocytosis and amyloid plaque formation. These neuropathological features have formed the basis of the histological diagnosis of human prion diseases for many years, although it was recognized that these changes are enormously variable both from case to case and within the central nervous system in individual cases.

Transmissible spongiform encephalopathies encompass the following diseases (including natural host and prion name): scrapie (sheep and goats; scrapie prion); transmissible mink encephalopathy (TME) (mink; TME prion); chronic wasting disease (CWD) (elk, white-tailed deer, mule deer and red deer; CWD prion); bovine spongiform encephalopathy (BSE) commonly known as "mad cow disease" (cattle; BSE prion); feline spongiform encephalopathy (FSE) (cats; FSE prion); Exotic ungulate encephalopathy (EUE) (nyala and greater kudu; EUE prion); kuru (human; Kuru prion); Creutzfeldt-Jakob disease (CJD) or Variant Creutzfeldt-Jakob disease (vCJD, nvCJD) (human; CJD and vCJD prions); Gerstmann-Sträussler-Scheinker syndrome (GSS) (human; GSS prion); and fatal familial insomnia (FFI) (human; FFI prion).

SOD1

Superoxide dismutase (SOD1) is an enzyme that in humans is encoded by the SOD1 gene, located on chromosome 21. SOD1 is one of three human superoxide dismutases. It is implicated in apoptosis (programmed cell death) and amyotrophic lateral sclerosis (ALS). The SOD1 gene provides instructions for making an enzyme called superoxide dismutase, which is abundant in cells throughout the body. This enzyme binds to molecules of copper and zinc to break down toxic, charged oxygen molecules called superoxide radicals. The molecules are byproducts of normal cell processes, and they must be broken down regularly to avoid damaging cells. Mutations in the gene for the enzymes superoxide dismutase 1 (SOD1) or copper zinc superoxide dismutase have been found in approximately 15-20 percent of the familial cases of ALS. SOD1 is also pivotal in reactive oxygen species (ROS) release during oxidative stress by ischemia-reperfusion injury, specifically in the myocardium as part of a heart attack (also known as ischemic heart disease). Ischemic heart disease results from an occlusion of one of the major coronary arteries. During ischemia reperfusion, ROS release substantially contribute to cell damage and death via a direct effect on the cell as well as via apoptotic signals. SOD1 is known to have a capacity to limit the detrimental effects of ROS. As such, SOD1 is important for its cardioprotective effects. In addition, SOD1 has been implicated in cardioprotection against ischemia-reperfusion injury, such as during ischemic preconditioning of the heart. Although a large burst of ROS is known to lead to cell damage, a moderate release of ROS from the mitochondria, which occurs during nonlethal short episodes of ischemia, can play a significant triggering role in the signal transduction pathways of ischemic preconditioning leading to reduction of cell damage HD, Htt Huntington's disease (HD) is a type of dementia caused by an inherited defect in a single gene on chromosome 4. Huntington's disease is an autosomal dominant disorder, which means that a person needs only one copy of the defective gene to develop the disorder. The defective gene codes for a protein known as huntingtin, which in turn leads to brain changes that cause abnormal involuntary movements, a severe decline in thinking and reasoning skills, and irritability, depression and other mood changes. Huntington's disease also causes a decline in thinking and reasoning skills, including memory, concentration, judgment and ability to plan and organize.

TDP-43

Almost all cases of ALS as well as tau-negative frontotemporal dementia (FTD) share a common neuropathology characterized by the deposition of TAR-DNA binding protein (TDP)-43-positive protein inclusions. A hyper-phosphorylated, ubiquitinated and cleaved form of TDP-43 (known as pathologic TDP43) is the major disease protein in ubiquitin-positive, tau-, and alpha-synuclein-negative frontotemporal dementia and in ALS. Elevated levels of the TDP-43 protein have also been identified in individuals diagnosed with chronic traumatic encephalopathy, a condition that often mimics ALS and that has been associated with athletes who have experienced multiple concussions and other types of head injury. Abnormalities of TDP-43 also occur in an important subset of Alzheimer's disease patients.

C9orf72

Mutations of another protein found in many regions of the brain, CRorf72, have been found to be a genetic link between familial frontotemporal dementia (FTD) and ALS. The C9orf72 gene is located on the short (p) arm of chromosome 9 at position 21.2. The mutation of C9ORF72 is a hexanucleotide repeat expansion of the six-letter string of nucleotides GGGGCC. In healthy humans, there are few repeats of this hexanucleotide, but in people with the mutation, the repeat can occur in the order of hundreds. It is known that the mutation interferes with normal expression of the protein made by C9orf72. C9orf72 can cause FTD and/or ALS via accumulation of RNA in the nucleus and cytoplasm which becomes toxic, and RNA binding protein sequestration occurs. A truncated gene that only codes for half of the C9ORF72 protein can also cause the diseases. Additionally, RNA transcribed from the C9ORF72 gene, containing expanded GGGGCC repeats, is translated through a non-ATG initiated mechanism. This drives the formation and accumulation of dipeptide repeat proteins corresponding to multiple ribosomal reading frames on the mutation. GGGGCC repeat expansion in C9orf72 compromises nucleocytoplasmic transport.

Despite the attention of many established and new ventures seeking treatment of neurodegenerative conditions and diseases, there is a long-felt need to develop a treatment for human patients to not only treat the symptoms of a neurodegenerative disease (such as Alzheimer's), but also to develop a treatment that can prevent healthy humans from developing such neurodegenerative diseases or treat sick patients to reverse, stop or slow the course of such neurodegenerative diseases.

SUMMARY OF THE INVENTION

It is therefore an object of the invention to provide a method for treating healthy humans in order to prevent or slow the development of a neurodegenerative disease. Further it is an object of the invention to provide a method for treating sick patients in order to reverse, stop or slow the course of a neurodegenerative disease.

It is an object of the invention to provide a method for preventing or treating Alzheimer's disease, Tauopathies, Frontotemporal Dementia, Down Syndrome, Parkinson's and alpha-synucleopathies, Prion's disease, Huntington's disease, Amyloid Lateral Sclerosis, and other dementias and neurodegenerative disorders.

It is a further object of the invention to provide a method for preventing or treating other disease states, including but not limited to cancer, cardiovascular, heart, lung, kidney and/or liver homeostasis diseases, and the like.

It is a further object of the invention to provide a method for preventing or treating metal dis-homeostasis in various tissues (e.g., brain, heart, lung, kidney, liver, etc.).

It is a further object of the invention to provide a method for preventing, treating iron dis-homeostasis in various tissues (e.g., brain, heart, lung, kidney, liver, etc.).

In accordance with the above objects and others, the present invention is directed in part to a method of maintaining (heavy) metal homeostasis in healthy humans or restoring (heavy) metal homeostasis in sick human patients, comprising or consisting of chronically administering to the human(s) a pharmaceutical composition comprising or consisting of a therapeutically effective amount of Posiphen, active metabolites of Posiphen, therapeutically effective analogues of Posiphen, pharmaceutically acceptable salts and complexes thereof-together with one or more pharmaceutically acceptable excipients. In certain preferred embodiments, the metal is iron. In certain preferred embodiments, a therapeutically effective amount of the pharmaceutical composition is administered to maintain heavy metal homeostasis in the healthy human or restore heavy metal homeostasis in the sick human patient. In certain embodiments, Posiphen is administered in an amount from about 1 mg to less than about 200 mg. In certain embodiments, Posiphen is administered orally in an amount from about 1 mg to less than about 200 mg, preferably on a once a day basis. In certain preferred embodiments, Posiphen is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, and numbers in between these numbers, and all further integers to less than about 200 mg, preferably on a once a day basis. In certain embodiments, this dose is administered orally. In other embodiments, this dose is administered parenterally. In certain embodiments, Posiphen is administered orally in a dose from about 0.1 to about 30 mg (e.g., from about 0.14 mg to about 28.57 mg). In certain embodiments, Posiphen is administered intravenously in a dose from about 0.1 to about 30 mg (e.g., from about 0.14 mg to about 28.57 mg), or may be administered intraperitoneally in a dose from about 0.2 mg to about 40 mg. In certain embodiments, the invention is directed to maintaining (heavy) metal homeostasis in healthy humans. In other embodiments, the invention is directed to restoring (heavy) metal homeostasis in sick human patients.

The present invention is also directed to a method of preventing, stopping, slowing or delaying the onset of a neurodegenerative disease or condition in a healthy human or healthy humans or in a sick human patient or sick human patients, comprising or consisting of chronically administering to the human(s) a pharmaceutical composition consisting of a therapeutically effective amount of Posiphen, active metabolites of Posiphen, therapeutically effective analogues of Posiphen, pharmaceutically acceptable salts and complexes thereof, together with one or more pharmaceutically acceptable excipients. In certain embodiments, the method prevents, slows or delays the onset of a neurodegenerative disease selected from the group consisting of Alzheimer's disease, Tauopathies, Parkinson's and alpha-synucleopathies, Prion's disease, Down Syndrome, Huntington's disease, Amyloid Lateral Sclerosis and other dementias and neurodegenerative disorders. Such dementias include, but are not limited to, Vascular dementia, Dementia with Lewy bodies (DLB), Mixed dementia, Frontotemporal dementia, Creutzfeldt-Jakob disease, Normal pressure hydrocephalus, and Wernicke-Korsakoff Syndrome. Other conditions which can be treated or slowed from causing hallmark symptoms of the condition include traumatic brain injury, chronic traumatic encephalopathy (CPE), vascular dementia, posterior cortical atrophy (PCA), and the like. In certain preferred embodiments, a therapeutically effective amount of the pharmaceutical composition is administered to maintain heavy metal homeostasis in the healthy human or restore heavy metal homeostasis in the sick human patient suffering from a neurodegenerative disease. In certain embodiments, Posiphen is administered in an amount from about 1 mg to less than about 200 mg. In certain embodiments, Posiphen is administered orally in an amount from about 1 mg to less than about 200 mg, preferably on a once a day basis. In certain preferred embodiments, Posiphen is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, and numbers in between these numbers, and all further integers to less than about 200 mg, preferably on a once a day basis. In certain embodiments, Posiphen is administered orally in a dose from about 0.1 to about 30 mg (e.g., from about 0.14 mg to about 28.57 mg). In certain embodiments, this dose is administered orally. In other embodiments, this dose is administered parenterally. In certain embodiments, Posiphen is administered intravenously in a dose from about 0.1 to about 30 mg (e.g., from about 0.14 mg to about 28.57 mg), or may be administered intraperitoneally in a dose from about 0.2 mg to about 40 mg.

The present invention is also directed to a method of preventing, slowing or delaying the onset of cancer in a healthy human or in a sick human patient suffering from a cancerous condition, comprising or consisting of chronically administering to the human(s) a pharmaceutical composition consisting of a therapeutically effective amount of Posiphen, active metabolites of Posiphen, therapeutically effective analogues of Posiphen, pharmaceutically acceptable salts and complexes thereof, together with one or more pharmaceutically acceptable excipients. In certain preferred embodiments, a therapeutically effective amount of the pharmaceutical composition is administered to maintain heavy metal homeostasis in the healthy human or restore heavy metal homeostasis in the sick human patient suffering from a cancerous condition. In certain embodiments, Posiphen is administered in an amount from about 1 mg to less than about 200 mg. In certain embodiments, Posiphen is administered orally in an amount from about 1 mg to less than about 200 mg, preferably on a once a day basis. In certain preferred embodiments, Posiphen is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, and numbers in between these numbers, and all further integers to less than about 200 mg, preferably on a once a day basis. In certain embodiments, this dose is administered orally. In other embodiments, this dose is administered parenterally. In certain embodiments, Posiphen is administered orally in a dose from about 0.1 to about 30 mg (e.g., from about 0.14 mg to about 28.57 mg). In certain embodiments, Posiphen is administered intravenously in a dose from about 0.1 to about 30 mg (e.g., from about 0.14 mg to about 28.57 mg), or may be administered intraperitoneally in a dose from about 0.2 mg to about 40 mg.

The present invention is also directed to a method of preventing, slowing or delaying the onset of cardiovascular disease or condition in a healthy human or in a sick human patient suffering from a cardiovascular disease or condition, comprising or consisting of chronically administering to the human(s) a pharmaceutical composition comprising or consisting of a therapeutically effective amount of Posiphen, active metabolites of Posiphen, therapeutically effective analogues of Posiphen, pharmaceutically acceptable salts and complexes thereof, together with one or more pharmaceutically acceptable excipients. In certain preferred embodiments, a therapeutically effective amount of the pharmaceutical composition is administered to maintain heavy metal homeostasis in the healthy human or restore heavy metal homeostasis in the sick human patient suffering from a cardiovascular disease or condition. In certain embodiments, Posiphen is administered in an amount from about 1 mg to less than about 200 mg. In certain preferred embodiments, Posiphen is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, and numbers in between these numbers, and all further integers to less than about 200 mg, preferably on a once a day basis. In certain embodiments, this dose is administered orally. In other embodiments, this dose is administered parenterally. In certain embodiments, Posiphen is administered orally in an amount from about 1 mg to less than about 200 mg, preferably on a once a day basis. In certain embodiments, Posiphen is administered orally in a dose from about 0.1 to about 30 mg (e.g., from about 0.14 mg to about 28.57 mg). In certain embodiments, Posiphen is administered intravenously in a dose from about 0.1 to about 30 mg (e.g., from about 0.14 mg to about 28.57 mg), or may be administered intraperitoneally in a dose from about 0.2 mg to about 40 mg.

The present invention is also directed to a method of maintaining cardiovascular homeostasis in a healthy human (or in a sick human patient(s) suffering from cardiovascular disease, comprising or consisting of chronically administering to the human(s) a pharmaceutical composition consisting of a therapeutically effective amount of Posiphen, active metabolites of Posiphen, therapeutically effective analogues of Posiphen, pharmaceutically acceptable salts and complexes thereof, together with one or more pharmaceutically acceptable excipients. In certain preferred embodiments, a therapeutically effective amount of the pharmaceutical composition is administered to maintain heavy metal homeostasis in the healthy human or restore heavy metal homeostasis in the sick human patient suffering from cardiovascular disease. In certain embodiments, Posiphen is administered in an amount from about 1 mg to less than about 200 mg. In certain embodiments, Posiphen is administered orally in an amount from about 1 mg to less than about 200 mg, preferably on a once a day basis. In certain preferred embodiments, Posiphen is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, and numbers in between these numbers, and all further integers to less than about 200 mg, preferably on a once a day basis. In certain embodiments, this dose is administered orally. In other embodiments, this dose is administered parenterally. In certain embodiments, Posiphen is administered orally in a dose from about 0.1 to about 30 mg (e.g., from about 0.14 mg to about 28.57 mg). In certain embodiments, Posiphen is administered intravenously in a dose from about 0.1 to about 30 mg (e.g., from about 0.14 mg to about 28.57 mg), or may be administered intraperitoneally in a dose from about 0.2 mg to about 40 mg.

The present invention is also directed to a method of maintaining homeostasis in vital organs in a healthy human or in a sick human suffering from a disease or condition in a vital organ, comprising or consisting of chronically administering to the human(s) a pharmaceutical composition consisting of a therapeutically effective amount of Posiphen, active metabolites of Posiphen, therapeutically effective analogues of Posiphen, pharmaceutically acceptable salts and complexes thereof, together with one or more pharmaceutically acceptable excipients. In certain embodiments, the vital organ is selected from, e.g., brain, heart, lung, liver, and/or kidney. In certain preferred embodiments, a therapeutically effective amount of the pharmaceutical composition is administered to maintain heavy metal homeostasis in the healthy human or restore heavy metal homeostasis in the sick human patient suffering from a disease in a vital organ. In certain embodiments, Posiphen is administered in an amount from about 1 mg to less than about 200 mg. In certain embodiments, Posiphen is administered orally in an amount from about 1 mg to less than about 200 mg, preferably on a once a day basis. In certain preferred embodiments, Posiphen is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, and numbers in between these numbers, and all further integers to less than about 200 mg, preferably on a once a day basis. In certain embodiments, this dose is administered orally. In other embodiments, this dose is administered parenterally. In certain embodiments, Posiphen is administered orally in a dose from about 0.1 to about 30 mg (e.g., from about 0.14 mg to about 28.57 mg). In certain embodiments, Posiphen is administered intravenously in a dose from about 0.1 to about 30 mg (e.g., from about 0.14 mg to about 28.57 mg), or may be administered intraperitoneally in a dose from about 0.2 mg to about 40 mg.

The invention also relates in part to a method of restoring heavy metal homeostasis in sick patient(s), comprising chronically administering to a sick patient a pharmaceutical composition comprising or consisting of a therapeutically effective amount of Posiphen, active metabolites of Posiphen, therapeutically effective analogues of Posiphen, pharmaceutically acceptable salts and complexes thereof, together with one or more pharmaceutically acceptable excipients. By virtue of this method, treatment of a potential disease state such as a neurodegenerative disease, cardiovascular homeostasis, cancer, vital organ homeostasis, and the like. In certain preferred embodiments, a therapeutically effective amount of the pharmaceutical composition is administered to restore heavy metal homeostasis in the sick human patient. In certain embodiments, Posiphen is administered in an amount from about 1 mg to less than about 200 mg. In certain embodiments, Posiphen is administered orally in an amount from about 1 mg to less than about 200 mg, preferably on a once a day basis. In certain preferred embodiments, Posiphen is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, and numbers in between these numbers, and all further integers to less than about 200 mg, preferably on a once a day basis. In certain embodiments, this dose is administered orally. In other embodiments, this dose is administered parenterally. In certain embodiments, Posiphen is administered orally in a dose from about 0.1 to about 30 mg (e.g., from about 0.14 mg to about 28.57 mg). In certain embodiments, Posiphen is administered intravenously in a dose from about 0.1 to about 30 mg (e.g., from about 0.14 mg to about 28.57 mg), or may be administered intraperitoneally in a dose from about 0.2 mg to about 40 mg. In certain preferred embodiments, the method results in amelioration of symptoms of the disease.

The invention further relates in part to a method of restoring heavy metal homeostasis to a mammal (e.g., a human) who has suffered an acute injury/incidence, including but not limited to traumatic brain injury, spinal cord injury, stroke, heart attack, acute glaucoma, near drowning, etc. in which the methods of the invention will further comprise or consist of chronically administering to the patient who has suffered an acute injury/incidence a pharmaceutical composition comprising or consisting of chronically administering a therapeutically effective amount of Posiphen, active metabolites of Posiphen, therapeutically effective analogues of Posiphen, pharmaceutically acceptable salts and complexes thereof, together with one or more pharmaceutically acceptable excipients. By virtue of this method, treatment of the acute injury/incidence preferably results in a stasis and/or amelioration of symptoms or effects of the acute injury/incidence. In certain embodiments, Posiphen is administered in an amount from about 1 mg to less than about 200 mg. In certain embodiments, Posiphen is administered orally in an amount from about 1 mg to less than about 200 mg. In certain preferred embodiments, Posiphen is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, and numbers in between these numbers, and all further integers to less than about 200 mg, preferably on a once a day basis. In other embodiments, Posiphen is administered parenterally. In such embodiments, Posiphen may be administered intravenously in a dose from about 0.1 to about 30 mg (e.g., from about 0.14 mg to about 28.57 mg), or may be administered intraperitoneally in a dose from about 0.2 mg to about 40 mg.

In certain embodiments, the invention is further directed to a kit comprising therapeutically effective doses of Posiphen (as set forth above), active metabolites of Posiphen, therapeutically effective analogues of Posiphen, pharmaceutically acceptable salts and complexes thereof, together with one or more pharmaceutically acceptable excipients or a pharmaceutically acceptable salt thereof together with one or more pharmaceutically acceptable excipients. In certain preferred embodiments, the kit is useful for the acute treatment of a mammal (e.g., a human patient) who has suffered an acute injury/incidence, including but not limited to traumatic brain injury, spinal cord injury, stroke, heart attack, acute glaucoma, near drowning, etc. The effective doses of Posiphen may be oral dosage forms (e.g., tablets or capsules), or injectable dosage forms. The kit can contain a device to administer Posiphen iv, ip, or im.

In certain preferred embodiments of each of the methods described above, the pharmaceutical composition includes from about 7.5 mg to less than about 200 mg of Posiphen or a pharmaceutically acceptable salt thereof.

In certain preferred embodiments of the above methods and kit, peak plasma circulating levels of Posiphen in the humans range, e.g., from about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL to about 160 ng/mL. In certain preferred embodiments, the peak plasma circulating level is reached within about 6 hours after administration of Posiphen to the humans. In certain preferred embodiments, the peak plasma circulating level is reached within about 3 hours after administration of Posiphen to the humans. In certain preferred embodiments, the plasma circulating level of Posiphen is equal to or greater than about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 mg/mL, 15 ng/mL, 16 ng/mL, 17 ng/mL, 18 ng/mL, 19 ng/mL, or 20 ng/mL for at least 9 hours, and preferably for at least 12 hours, after administration of Posiphen to the humans. In certain embodiments, the steady-state plasma concentration of Posiphen is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 ng/mL. In certain preferred embodiments, the half-life of Posiphen in cerebrospinal fluid after administering is about 12 hours, and the half-life of Posiphen in plasma after administering is about 5 hours. In certain preferred embodiments, the chronic of administration of Posiphen to the humans results in a brain level of Posiphen that ranges from about 4 to about 10 times the plasma level of Posiphen in those patients.

With respect to each of the methods described above, Posiphen or a pharmaceutically acceptable salt thereof may be administered, e.g., orally, parenterally, sublingually, via suppository, nasally, topically, transdermally, or via implant under the skin.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, the term "Posiphen®" is used interchangeably to refer to (3aR)-1,3a,8-trimethyl-1,2,3,3a,8,8a-hexahydropyrrolo[2,3-b]indol-5-ylphenylcarbamate or a salt thereof.

As used herein, the term "APP" refers to amyloid precursor protein.

As used herein, the term "Aβ" refers to amyloid-β peptide.

As used herein, the term "Tau" refers to any of the products of alternative splicing from the gene designated MAPT.

As used herein, the term "SNCA" refers to the gene for alpha-synuclein (aSYN)

As use herein, the term "NAC" refers to the alpha-synuclein fragment known as the non-A4 component (NAC) of Alzheimer's disease amyloid.

As used herein, the term "prion" refers to an infectious agent composed of protein in a misfolded form.

As used herein, the term "TSE" refers to any form or variety of a transmissible spongiform encephalopathy.

As used herein, the terms "alpha-synuclein" and "aSYN" are synonymous.

As used herein, the term "transmissible spongiform encephalopathy" and "TSE" are synonymous.

As used herein, the term "SOD1" refers to Superoxide dismutase (SOD1), which is an enzyme that in humans is encoded by the SOD1 gene, located on chromosome 21.

As used herein, the term "PD" refers to Parkinson's Disease.

As used herein, the term "DS" refers to Down Syndrome.

As used herein, the term "iron regulatory protein" is synonymous with "IRP"

As used herein, the term "iron-responsive element" is synonymous with "IRE".

As used herein, the term "HTT" refers to huntingtin or the Huntington protein.

As used herein, "TDP43" refers to the TAR-DNA binding protein TDP43.

As used herein, "C9orf72" refers to the C9orf72 protein found in many regions of the brain.

As used herein, the term "neurotoxic aggregating protein" refers to a protein or family of proteins that has neurotoxic effect upon accumulating in a tissue of the brain, such as the brain tissue. Non-limiting examples of neurotoxic aggregating proteins are APP, Aβ, SOD1, SNCA, NAC, TSE amyloid plaque, HTT, Tau, TDP43 and C9orf72.

As used herein, the terms "protein", "peptide" and "polypeptide" are used interchangeably, and refer to a compound comprised of amino acid residues covalently linked by peptide bonds.

By the term "specifically binds," as used herein, is meant a molecule, such as an antibody or a small molecule, which recognizes and binds to another molecule or feature, but does not substantially recognize or bind other molecules or features in a sample.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

"Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil;

glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds may also be incorporated into the compositions.

As used herein, the "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

The term "treat" or "treating", as used herein, means reducing the frequency with which symptoms are experienced by a subject or administering an agent or compound to reduce the frequency and/or severity with which symptoms are experienced. As used herein, "alleviate" is used interchangeably with the term "treat." Treating a disease, disorder or condition may or may not include complete eradication or elimination of the symptom. The term "therapeutic" as used herein means a treatment and/or prophylaxis of a condition or disease state as described herein.

As used herein, the term "sick patient" means a mammal (e.g., human) who is suffering from disease state such as a neurodegenerative disease, cardiovascular homeostasis, cancer, vital organ homeostasis, and the like.

As used herein, the term "healthy human" means a mammal (e.g., human) who is not presently suffering from a disease state caused by metal dis-homeostasis, such as a neurodegenerative disease, cardiovascular disease, cancer, vital organ disfunction, and the like, but may be at risk of suffering from such a disease in the future.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 11 is a graph showing the effect of Posiphen in neuroblastoma cells on

FIG. 16 is a table with a Western Blot showing that Posiphen inhibits aSYN in the enteric nervous system of transgenic PD animals;

FIG. 17 is a table showing a decline of APP and its fragments as well as tau in the hippocampus of APP/PS1 transgenic AD animals;

FIG. 18a is a graph showing a decrease in aggregated tau in the hippocampus of APP transgenic AD animals (DA31 insoluble);

FIG. 18b is a graph showing a decrease in aggregated tau in the hippocampus of APP transgenic AD animals (CP13 insoluble);

FIG. 18c is a graph showing a decrease in aggregated tau in the hippocampus of APP transgenic AD animals (RZ3 insoluble);

FIG. 18d is a graph showing a decrease in aggregated tau in the hippocampus of APP transgenic AD animals (PHF1 insoluble);

DETAILED DESCRIPTION OF THE INVENTION

Figure 1:
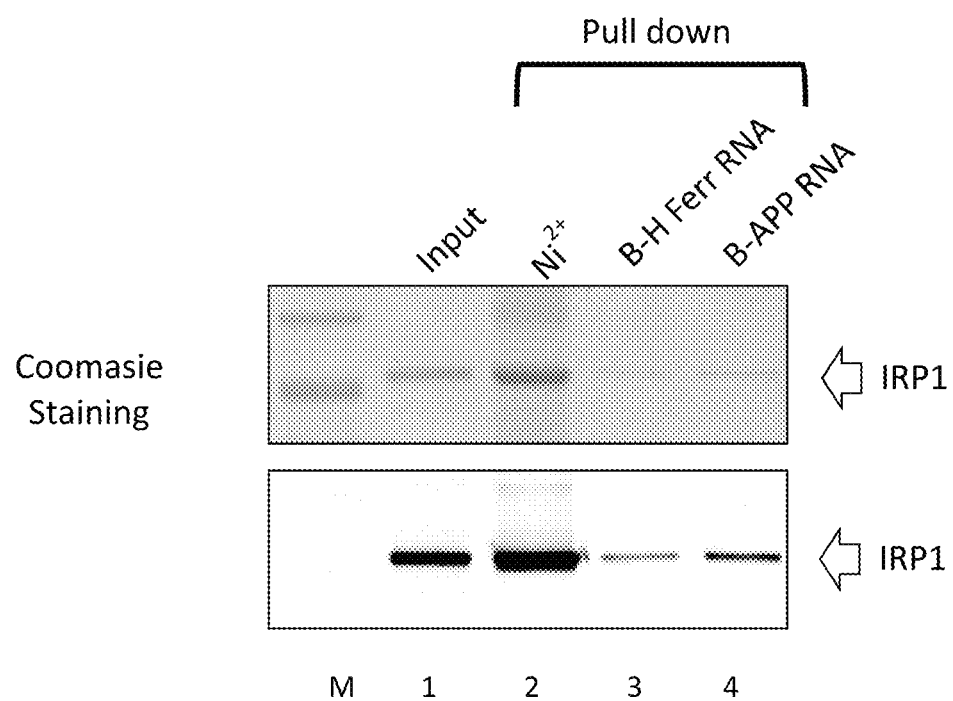
FIG. 1 is a depiction of a Western Blot showing the binding of the IRP1-H-Ferritin and IRP1-APP complexes.

Iron is a vital element in humans and is a constituent of a number of important macromolecules, including those involved in energy production, respiration, DNA synthesis, and metabolism. Iron is a trace element of crucial importance to living cells that exists in a divalent state. Because of its divalent nature, iron may act as a redox component of proteins, and therefore is integral to vital biologic processes that require the transfer of electrons. It is intimately involved in numerous vital biologic processes, including oxygen transport, oxidative phosphorylation, DNA biosynthesis, and xenobiotic metabolism. All cells use some iron. Too much or too little "labile iron" has been recognized as a cause or consequence of many human disease states. Iron overload leads to a number of different pathologies, including structural damage from physical iron accumulation and oxidative damage to tissue, protein, lipids, and DNA resulting from iron-induced oxidative stress. Therefore, maintaining proper "labile iron" levels has been recognized as important in preserving homeostasis in humans.

Cellular iron homeostasis is maintained by iron regulatory proteins 1 and 2 (IRP1 and IRP2), and the activity of IRP1 and IRP2 is controlled by iron levels in the cell. IRPs bind to iron-responsive elements (IREs) located in the untranslated regions of mRNAs encoding proteins involved in iron uptake, storage, utilization and export. When cells are iron deficient, IRPs bind to 5' IREs in ferritin and ferroportin mRNAs with high affinity to repress translation, and to 3' IREs in TfR1 mRNA to block its degradation. When iron is in excess, IRPs do not bind to IREs, increasing synthesis of ferritin and ferroportin, while promoting the degradation of TfR1 mRNA. The coordinated regulation of iron uptake, storage and export by the IRPs ensures that cells acquire adequate iron for their needs without reaching toxic levels.

Under steady-state conditions or homeostasis, the mRNA of APP is bound to the iron regulatory protein 1 (IRP1) through a stem loop in its 5' untranslated region (5'UTR). This stem loop is called iron-responsive element (IRE). When IRP1 is bound to the stem loop, it prevents the complex from binding to the ribosome and prevents translation of the mRNA (Venti 2004; Cahill 2009; Cho 2010; Rogers 2011).

At increased iron levels, the APP mRNA stem loop is released from IRP1 and the mRNA is moved to the ribosome, where it is translated. In normal cell division, ferritin shuttles iron in and out of the cell during the cell cycle, so that APP is produced when the cell divides and returns to binding to IRP1, when the cell is stationary. Upon insult, iron flows into the cell, but the iron levels remain high and APP is synthesized to high levels and remains at these elevated levels, therefore, turning toxic.

Posiphen®, developed by QR Pharma, Inc., is a small molecule that lowers soluble APP protein levels through a post-transcriptional mechanism. Posiphen is a selective inhibitor of amyloid precursor protein (APP) production and has potential utility as a disease modifying treatment for AD (Cullen 2006; Utsuki 2006; Lahiri 2007). Posiphen was discovered at the National Institute on Aging and was selected from a series of structurally related compounds designed for APP specificity with no or minimal acetylcholinesterase inhibitory activity. Posiphen was shown to reduce APP and consequently beta-amyloid (Aβ) production in relevant preclinical in vitro and in vivo studies. Maccecchini, et al., Posiphen as a Candidate Drug to Lower CSF Amyloid Precursor Protein, Amyloid-β Peptide and τ Levels: Target Engagement, Tolerability and Pharmacokinetics in Humans", J. Neurosurg. Psychiatry 2012; 83:894-902, hereby incorporated by reference, reported the results of a study of Posiphen single and multiple ascending dose phase 1 randomised, double blind, placebo controlled safety, tolerance, pharmacokinetic studies were undertaken in 120 healthy human volunteers to define a dose that was then used in a small non-randomised study of five MCI subjects. Posiphen doses up to 4×60 mg daily×10 days were well tolerated. In plasma Posiphen, at all doses, was absorbed rapidly (Tmax=1.2 to 1.7 h) and cleared from the circulation biphasically (terminal half-life of 4.3-4.7 h). Posiphen proved well tolerated and significantly lowered CSF levels of sAPPα, sAPPβ, t-tau, p-tau and specific inflammatory markers, and demonstrated a trend to lower CSF $A\beta_{42}$. Posiphen's activity is also described in Applicant's co-pending U.S. patent application Ser. No. 13/041,211 (filed Mar. 4, 2011), hereby incorporated by reference.

Posiphen is the steroisomer of Phenserine (−)-N-phenyl-carbamoyl eseroline), which reached clinical assessment for AD as an anticholinesteraseinhibitor. Posiphen is also known as (+)-Phenserine. Phenserine is an AChE inhibitor which has been investigated as being suitable as an agent for therapy for cognitive impairments associated with aging and Alzheimer's disease (U.S. Pat. No. 5,409,948). In 2004, it was reported that Phenserine was most efficient to block translation of APP mRNA under conditions of intracellular iron chelation with desferrioxamine, suggesting that this anticholinesterase operated through an iron (metal)—dependent pathway at the APP 5'-UTR site. (Venti, et al. "The Integrated Role of Desferrioxamine and Phenserine Targeted to an Iron-Responsive Element in the APP-mRNA 5-Untranslated Region", Ann. N.Y. Acad. Sci. 1035: 34-48 (2004), hereby incorporated by reference in its entirety. This would mean that Phenserine works at low iron levels. However, this was exactly the opposite of what was found by the present inventor.

In Lahiri, et al., "The Experimental Alzheimer's Disease Drug Posiphen [(+)-Phenserine] Lowers Amyloid-β Peptide Levels in Cell Culture and Mice", J. Pharmacol. Ther. 320:386-396, 2007 (hereby incorporated by reference), the authors reported that Posiphen reduces newly synthesized APP without altering APP mRNA or total protein synthesis. Therein, administration of Posiphen (10 and 50 µM) and phenserine (50 µM) to human neuroblastoma cell line SK-N-SH reduced intracellular and secreted levels of APP at 16 hours as quantified by Western blot analysis. To define concentration dependence, and SH-SY-5Y neuroblastoma cells were treated for 16 hours with Posiphen, phenserine or vehicle and intracellular levels of APP were quantified. Both agents induced a similar concentration-dependent decline in APP levels by approximately 50%, beyond which increases in dose resulted in no further APP reductions. Posiphen was reported to significantly lower $A\beta_{40}$ levels in mouse cerebral cortex at a dose of 7.5 mg/kg, and higher doses induced further dose-dependent declines to a maximal 40% drop. All doses of Posiphen were reported to significantly reduced brain $A\beta_{42}$ levels by up to 58% for Posiphen (25 mg/kg), albeit with no apparent dose dependence. Thus, this paper reports that Posiphen inhibits APP by 50% in neuroblastoma cells as well as in healthy mice.

In Rogers, et al., "The alpha-synuclein 5' untranslated region targeted translation blockers: anti-alpha synuclein efficacy of cardiac glycosides and Posiphen" J. Neural Transm, published online 8 Jan. 2011 (hereby incorporated by reference), Posiphen was identified to repress SNCA 5'UTR conferred translation. Western blotting confirmed that Posiphen and the cardiac glycoside, strophanthidine, selectively blocked SNCA expression in neural cells. For Posiphen this inhibition was accelerated in the presence of iron, thus providing a known APP-directed lead with potential for use as a SNCA blocker for PD therapy. This publication reports that Posiphen inhibits APP and alpha-synuclein and speculates that it does so by increasing the binding of the aSYN mRNA to IRP1. [Sohan Mikkilineni, Ippolita Cantuti-Castelvetri, Catherine M. Cahill, Amelie Balliedier, Nigel H. Greig, and Jack T. Rogers. The Anti-cholinesterase Phenserine and Its Enantiomer Posiphen as 5' Untranslated-Region-Directed Translation Blockers of the Parkinson's Alpha Synuclein Expression; Parkinson's Disease; Volume 2012, Article ID 142372, 13 pages; doi: 10.1155/2012/142372] (hereby incorporated by reference).

Posiphen, phenserine's better-tolerated (+) enantiomer (devoid of anticholinesterase action), repressed neural alpha-synuclein translation. Primary metabolic analogs of Posiphen were, likewise, characterized using primary fetal neurons grown ex vivo from the brains of Parkinson's transgenic mice expressing the human SNCA gene.

More recently, Bandyopadhyay, et al., "Novel 5' Untranslated Region Directed Blockers of Iron-Regulatory Protein-1 Dependent Amyloid Precursor Protein Translation: Implications for Down Syndrome and Alzheimer's Disease", [Sanghamitra Bandyopadhyay, Catherine Cahill, Amelie Balleidier, Conan Huang, Debomoy K. Lahiri,[3] Xudong Huang, and Jack T. Rogers[1] Novel 5' Untranslated Region Directed Blockers of Iron-Regulatory Protein-1 Dependent Amyloid Precursor Protein Translation: Implications for Down Syndrome and Alzheimer's Disease; PLoS One. 2013; 8(7): e65978. Published online 2013 Jul. 31, 2013 (hereby incorporated by reference) reported that iron influx drives the translational expression of the neuronal amyloid precursor protein (APP). This is via a classic release of repressor interaction of APP mRNA with iron-regulatory protein-1 (IRP1) whereas IRP2 controls the mRNAs encoding the L- and H-subunits of the iron storage protein, ferritin.

The present inventor was able to reproduce results indicating that Posiphen inhibits APP and aSYN in neuroblastoma cells. However, it has now been unexpectedly found that Posiphen does not inhibit translation of neurotoxic aggregating proteins in healthy mouse brain, or in fully differentiated healthy resting nerve cells. Under iron or metal-homeostasis, Posiphen does not increase the binding of APP or aSYN mRNA to IRP1. Therefore, the original data concerning the effects of Posiphen working under all conditions is wrong. It only works in stressed cells, dividing cells and sick cells, e.g., those cells that have high levels of iron.

Posiphen augments the binding of APP mRNA IRE to IRP1 under high iron conditions and prevents APP from being translated excessively, restoring homeostasis. The same mechanism works for all neurotoxic aggregating proteins tested to date: Posiphen works under iron-dishomeostasis to restore homeostasis.

It has further been surprisingly discovered that Posiphen does not have any effect on normal, healthy cells—where the level of iron is also normal. Once this discovery was made, the activity of Posiphen in a variety of cells made sense: in fully differentiated nerve cells that do not divide, administration of Posiphen elicits no effect. In dividing cells, the iron levels go up and down with the cell cycle. Posiphen inhibits neurotoxic aggregating proteins in stem cells (dividing cells), but not in the differentiated neurons derived from the same. In the hippocampus of the brain of AD mice, where plaque accumulation occurs, Posiphen has been found to inhibit neurotoxic aggregating proteins. Areas where plaque accumulation occurs contain stressed and sick cells, which have high iron levels. On the other hand, areas where plaque is not typically found (until late in the disease state), such as the cerebral cortex, do not have high levels of iron, and Posiphen has now been found to not inhibit neurotoxic aggregating proteins in the cerebral cortex of transgenic AD and PD animals, although it inhibits these neurotoxic aggregating proteins in the hippocampus of AD animals and the enteric nerves of PD animals (i.e., in the gut), respectively.

Thus, the present invention is based on the fact that Posiphen works only in dividing, sick or stressed cells, where iron levels are high. For purposes of the present invention, iron levels in vitro are defined as follows: about 1 uM or lower=low iron levels; about 3 to about 10 uM=normal iron levels; from about 10 to about 100 uM=high iron levels. Iron levels in vivo are very difficult to measure and there is a lot of disagreement among the experts in defining what a high level is, because of very little free iron in vivo in humans. Depending on the extraction conditions levels, the value can vary by more than, e.g., 10-fold. However, there is some consensus: from imaging studies, diseased tissues show about twice as much iron as healthy tissues, or an increase, e.g., from about 50% to about 100% as compared to healthy tissues. From actual measurements in normal substantia nigra wet weight: 0.3 uM/gram of brain; dry weight: 13 uM/gram comparing in vitro with in vivo, 1 uM is about 0.05 uM/gram; 10 uM is about 0.5 uM/gram; and 50 uM is about 2.5 uM/gram.

The invention is directed in part to the treatment of healthy humans with chronic administration of effective amounts of Posiphen, its active metabolites, and pharmaceutically acceptable salts and complexes thereof, as well as analogues thereof. By virtue of the present invention, healthy humans can be treated with such drugs without any apparent effect—as long as they are healthy. It is only when cells in the body become stressed—e.g., have an abnormally high level of iron, that Posiphen will have a therapeutic effect, which will be to return the cells to normal iron levels, thereby avoiding the toxic levels that are found in a variety of disease states and conditions. In certain embodiments, the high iron levels in cells treated by the inventive methods include high iron levels caused by the onset of a neurodegenerative disease selected from the group consisting of Alzheimer's disease, Tauopathies, Parkinson's and alpha-synucleopathies, Prion's disease, Down Syndrome, Huntington's disease, Amyloid Lateral Sclerosis and other dementias and neurodegenerative disorders. Such dementias include, but are not limited to, Vascular dementia, Dementia with Lewy bodies (DLB), Mixed dementia, Frontotemporal dementia, Creutzfeldt-Jakob disease, Normal pressure hydrocephalus, and Wernicke-Korsakoff Syndrome. The invention is directed in part to the administration of Posiphen to healthy humans in order to prevent or control such neurological diseases, which have not as yet afflicted them. Other conditions which can be treated or slowed from causing hallmark symptoms of the condition include traumatic brain injury, chronic traumatic encephalopathy (CPE), vascular dementia, posterior cortical atrophy (PCA), and the like.

The invention also is directed to the treatment of healthy humans with chronic administration of effective amounts of Posiphen, its active metabolites, and pharmaceutically acceptable salts and complexes thereof, as well as analogues thereof for the prevention and control of diseases and conditions other than neurodegenerative disease. For example, it has now been demonstrated that Posiphen inhibits neurotoxic aggregating proteins in cancerous cells, and in Parkinson's disease and Down syndrome, e.g., diseases where the cells are stressed (e.g., have high heavy metal (iron) concentrations). Therefore, the treatment of healthy humans with Posiphen may prevent or control or delay or slow the onset of diseases such as Parkinson's and may prevent effects of Down syndrome by maintaining heavy metal homeostasis.

Further, it is known that other conditions in which the cells of the human patient are stressed (e.g., have high heavy metal concentrations such as iron), including but not limited to cardiovascular diseases or conditions of vital organs, and the like, may be prevented, controlled, delayed or slowed by the chronic administration of effective amounts of Posiphen to maintain heavy metal homeostasis. Thus, in certain embodiments the invention relates in part to a method of restoring heavy metal homeostasis in sick patient(s), comprising or consisting of chronically administering to a sick patient a pharmaceutical composition consisting of a therapeutically effective amount of Posiphen, a therapeutically effective amount of Posiphen, active metabolites of Posiphen, therapeutically effective analogues of Posiphen, pharmaceutically acceptable salts and complexes thereof, together with one or more pharmaceutically acceptable excipients, on a once a day basis. By virtue of this method, treatment of a potential disease state such as a neurodegenerative disease, cardiovascular homeostasis, cancer, vital organ homeostasis, and the like. In certain embodiments, Posiphen is administered in an amount from about 1 mg to less than about 200 mg. In certain embodiments, Posiphen is administered orally in an amount from about 1 mg to less than about 200 mg. In certain preferred embodiments, the method results in amelioration of symptoms of the disease.

As used herein, the term "Posiphen" refers to (3aR)-1,3a,8-trimethyl-1,2,3,3a,8,8a-hexahydropyrrolo[2,3-b]indol-5-ylphenylcarbamate, with the chemical structure shown in Formula I below, at a chemical purity of at least 90%, preferably at least 95%, at least 98%, at least 99%, at least 99.5%, at least 99.9% or 100%.

i.

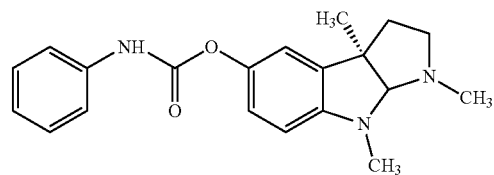

Formula I

The term "chemical purity" as applied to (3aR)-1,3a,8-trimethyl-1,2,3,3a,8,8a-hexahydropyrrolo[2,3-b]indol-5-yl phenylcarbamate or a pharmaceutically acceptable salt of Posiphen means the percent by weight of (3aR)-1,3a,8-trimethyl-1,2,3,3a,8,8a-hexahydropyrrolo[2,3-b]indol-5-yl phenylcarbamate or the pharmaceutically acceptable salt of Posiphen in terms of (3aR)-1,3a,8-trimethyl-1,2,3,3a,8,8a-hexahydropyrrolo[2,3-b]indol-5-yl phenylcarbamate or the pharmaceutically acceptable salt of Posiphen and other chemical impurities, e.g., its (−)-enantiomer, that may be present.

The compounds described herein may form salts with acids or bases, and such salts are included in the present invention. In one embodiment, the salts are pharmaceutically acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Examples of the pharmaceutically acceptable salt of Posiphen include acid addition salts prepared from a suitable acid. The suitable acid can be hydrobromic acid, hydrochloric acid, hydroiodic acid, sulfuric acid, carbonic acid, nitric acid, phosphoric acid, tetrafluoroboronic acid, perchloric acid, 1-hydroxy-2-naphthoic acid, 2,2-dichloroacetic acid, methanesulfonic acid, trifluoromethanesulfonic acid, 2-hydroxyethanesulfonic acid, benzenesulfonic acid, p-toluenesulfonic acid, cyclohexylaminosulfonic acid, 2-oxoglutaric acid, 4-acetamidobenzoic acid, acetic acid, phenylacetic acid, propionic acid, formic acid, succinic acid, glycolic acid, gluconic acid, malic acid, lactic acid, tartaric acid, citric acid, glucuronic acid, ascorbic acid, maleic acid, fumaric acid, pyruvic acid, aspartic acid, glutamic acid, benzoic acid, 4-hydroxybenzoic acid, anthranilic acid, 4-hydroxybenzoic acid, mandelic acid, pamoic acid, pantothenic acid, sulfanilic acid, stearic acid, alginic acid, β-hydroxybutyric acid, salicylic acid, galactaric acid and galacturonic acid. Preferably, the pharmaceutically acceptable salt is Posiphen tartrate, i.e., the acid addition salt of tartaric acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N methylglucamine) and procaine. Examples of pharmaceutically unacceptable base addition salts include lithium salts and cyanate salts. All of these salts may be prepared from the corresponding compound by reacting, for example, the appropriate acid or base.

The term "Posiphen" is also meant to encompass active metabolites of Posiphen. Active metabolites have previously been identified, e.g., in Applicant's U.S. Patent Publication No. and include, for example, "$N^1$-nor-Posiphen" (which refers to (3aR)-3a,8-dimethyl-1,2,3,3a,8,8a-hexahydropyrrolo[2,3-b]indol-5-ylphenylcarbamate) or a salt thereof; "$N^8$-nor-Posiphen" (which refers to (3aR)-1,3a-dimethyl-1,2,3,3a,8,8a-hexahydropyrrolo[2,3-b]indol-5-ylphenylcarbamate) or a salt thereof; and "$N^1,N^8$-nor-Posiphen" (which refers to (3aR)-3a-methyl-1,2,3,3a,8,8a-hexahydropyrrolo[2,3-b]indol-5-yl phenylcarbamate) or a salt thereof.

In other embodiments, the methods of the present invention are practiced using a phenserine or phenserine-like compound, metabolite, enantiomer, or derivative thereof, known to those skilled in the art, such as those described in U.S. Pat. Nos. 5,171,750; 6,410,747; 6,683,105, 7,153,882; 7,786,162; 7,973,057; 8,258,172; 8,546,430; 8,691,864; and 8,853,253, all of which are incorporated by reference in their entireties.

Chronic Administration

In the present invention, Posiphen, or a pharmaceutically acceptable salt of Posiphen, is administered chronically, e.g., on a once a day basis, in order to maintain homeostasis of metal (e.g., iron) levels in, e.g., vital organs in a healthy human patient(s). In certain embodiments, Posiphen is chronically administered to healthy humans who are in danger of or who might have a predisposition to a neurodegenerative disease, or cardiovascular disease, or a cancer. Posiphen, or a pharmaceutically acceptable salt of Posiphen, can also be administered once, twice, three times or four times daily. However, for chronic administration as preferred for the methods of the present invention, Posiphen is preferably administered on a once-a-day basis. Depending on the routes of administration, Posiphen can be administered in different dose ranges. For example, in some of the embodiments of the methods of the invention, Posiphen is administered orally in an amount from about 1 mg to less than about 200 mg. In some of the embodiments of the methods of the invention, Posiphen is administered intraocularly at 0.001 to 0.2 mg/kg body weight, preferably at 0.002 to 0.1 mg/kg body weight, or 0.005 to 0.05 mg/kg body weight. Posiphen may also be administered intravenously in a dose from about 0.1 to about 30 mg (e.g., from about 0.14 mg to about 28.57 mg), or may be administered intraperitoneally in a dose from about 0.2 mg to about 40 mg. When a pharmaceutically acceptable salt of Posiphen is administered in a method of the invention, the appropriate dose of the pharmaceutically acceptable salt of Posiphen administered can be calculated based on the dose of Posiphen disclosed herein using the ratio of the molecular weight of Posiphen and the molecular weight of the pharmaceutically acceptable salt of Posiphen so that the amount of the pharmaceutically acceptable salt of Posiphen administered would deliver a dose equivalent to the dose of Posiphen disclosed herein.

In general, the dose of Posiphen preferred to be administered to healthy human patients is a tolerable dose, i.e., a dose that does not cause untoward side effects in a majority of human patient, which dose is also effective for prophylactic treatment of the healthy human(s) with respect to, e.g., neurodegenerative diseases, cancer, cardiovascular homeostasis, diseases or conditions of vital organs, cardiovascular disease, and the like. Such doses have been found to comprise a Posiphen dose from about 3 mg to less than about 200 mg, per day.

In the methods of the invention, Posiphen can be administered parenterally or enterally. Examples of the route of administration of Posiphen are intravenous, intraocular, intramuscular, subcutaneous, topical, oral, sublingual and buccal. Preferably, for purposes of the present invention, Posiphen is administered orally.

In certain embodiments, the methods of the present invention further include administering a second pharmaceutically active agent for the purpose of prophylactically treating the human to prevent, slow or delay a disease state or condition as described herein. In such embodiments, the invention is further is directed to a packaged pharmaceutical composition comprising a container holding a therapeutically effective amount of Posiphen or other compound in accordance with the invention, alone or in combination with a second pharmaceutical agent; and instructions for using the composition to treat, prevent, or reduce one or more symptoms of a disease in a subject.

Iron Levels in Neurodegeneration and Other Conditions

Appropriate iron levels are especially important in the brain. Adequate iron levels are required for the increased respiration, neurotransmitter production, and myelinogenesis. Iron deficiency may have deleterious effects on neurotransmission, myelination, and dopamine receptor and transporter functions. On the other hand, excess iron concentrations are particularly harmful because the highly oxidative microenvironment of the brain lends itself to the production of ROS. Although brain iron regulation and uptake is not fully understood, many of the proteins involved in iron homeostasis throughout the body are also present in the brain, and increased brain iron levels have been observed in Alzheimer's disease and Parkinson's disease. Abnormal iron metabolism has also been implicated in the pathogenesis of neurodegeneration. Thus, excess iron content in the brain is associated with several inherited neurodegenerative diseases, including neurodegeneration with brain iron accumulation (NBIA) and Friedreich's ataxia (FA), as well as common neurodegenerative disorders such as Parkinson's and Alzheimer's diseases.

For example, Rogers, et al. (Biochem Soc Trans. 2008 December; 36 (Pt 6): 1282-7, "Iron and the translation of the amyloid precursor protein (APP) and ferritin mRNAs: riboregulation against neural oxidative damage in Alzheimer's disease.") reported that the essential metals iron, zinc and copper deposit near the Aβ plaques in the brain cortex of AD patients. In health, ubiquitous APP is cleaved in a non-amyloidogenic pathway within its Abeta domain to release the neuroprotective APP ectodomain, soluble APPs. To adapt and counteract metal-catalysed oxidative stress, as during reperfusion from stroke, iron and cytokines induce the translation of both APP and ferritin (an iron storage protein) by similar mechanisms. Rogers, et al. reported that APP was regulated at the translational level by active IL (interleukin)-1 (IL-1-responsive acute box) and IRE (iron-responsive element) RNA stem-loops in the 5' untranslated region of APP mRNA, and that the APP IRE is homologous with the canonical IRE RNA stem-loop that binds the iron regulatory proteins (IRP1 and IRP2) to control intracellular iron homoeostasis by modulating ferritin mRNA translation and transferrin receptor mRNA stability. The APP IRE interacts with IRP1 (cytoplasmic cis-aconitase), whereas the canonical H-ferritin IRE RNA stem-loop binds to IRP2 in neural cell lines, and in human brain cortex tissue and in human blood lysates. The same constellation of RNA-binding proteins [IRP1/IRP2/poly(C) binding protein] control ferritin and APP translation with implications for the biology of metals in AD.

Iron Levels in Cancer

Iron levels have been implicated in cancer. Researchers have reported that iron is critical for growth of tumors (Torti, et al. "Ironing out cancer", Cancer Res., 71 (2011), pp. 1511-1514). Tumor cells can satisfy their increased need for iron by increasing TfR1 expression as well as reducing ferritin and ferroportin expression (See, e.g., Cozzi, et al. "Overexpression of wild type and mutated human ferritin H-chain in HeLa cells: in vivo role of ferritin ferroxidase activity", J. Biol. Chem., 275 (2000), pp. 25122-25129; Kakhlon, et al., "Repression of ferritin expression increases the labile iron pool, oxidative stress, and short-term growth of human erythroleukemia cells", Blood, 97 (2001), pp. 2863-2871; Cozzi, et al., "Analysis of the biologic functions of H- and L-ferritins in HeLa cells by transfection with siRNAs and cDNAs: evidence for a proliferative role of L-ferritin", Blood, 103 (2004), pp. 2377-2383; Baldi, et al., "Ferritin contributes to melanoma progression by modulating cell growth and sensitivity to oxidative stress", Clin. Cancer Res., 11 (2005), pp. 3175-3183; Pinnix, et al., "Ferroportin and iron regulation in breast cancer progression and prognosis", Sci. Transl. Med., 2 (2010), p. 43ra56). IRP2 has also been shown to have a role in cell proliferation. For example, researchers have demonstrated that IRP2 overexpression in H1299 lung cancer cells stimulated their ability to form tumors when grown as xenografts in immunodeficient mice, whereas overexpression of IRP2 lacking the 73-amino acid domain suppressed tumor xenograft growth, suggesting a unique function for this domain (Maffettone, "Tumorigenic properties of iron regulatory protein 2 (IRP2) mediated by its specific 73-amino acids insert", PLoS One, 5 (2010), p. e10163). In contrast, researchers have also demonstrated that overexpression of IRP1 in H1299 lung cancer cells suppressed tumor xenograft growth in mice (Chen, et al., "Overexpression of iron regulatory protein 1 suppresses growth of tumor xenografts", Carcinogenesis, 28 (2007), pp. 785-791).

In the methods of the invention, the subject treated is a mammal, preferably a human.

Pharmaceutical Compositions and Therapies

Administration of a compound useful within the invention may be achieved in a number of different ways, using methods known in the art. The therapeutic and prophylactic methods of the invention thus encompass the use of pharmaceutical compositions comprising the compounds useful within the invention to practice the methods of the invention. The pharmaceutical compositions useful for practicing the invention may be administered to deliver a dose of 1 ng/kg/day to 100 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Typically, dosages which may be administered in a method of the invention to an animal, preferably a human, range in amount from 0.5 µg to about 50 mg per kilogram of body weight of the animal. While the precise dosage administered will vary depending upon any number of factors, including but not limited to, the type of animal and type of disease state being treated, the age of the animal and the route of administration, the dosage of the compound will preferably vary from about 1 μg to about 10 mg per kilogram of body weight of the animal. More preferably, the dosage will vary from about 3 μg to about 1 mg per kilogram of body weight of the animal.

Pharmaceutical compositions that are useful in the methods of the invention may be prepared, packaged, or sold in formulations suitable for oral, parenteral, topical, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The composition of the invention may consist of the active ingredient alone, in a form suitable for administration to a (human) subject or patient, or the composition may comprise at least one active ingredient and one or more pharmaceutically acceptable excipients.

In one embodiment, the compositions of the invention are formulated using one or more pharmaceutically acceptable carriers. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey). The carrier may be a solvent or dispersion medium containing, for example, water, ethanol, polyol (for example, glycerol, propylene glycol, and liquid polyethylene glycol, and the like), suitable mixtures thereof, and vegetable oils.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

Controlled- or sustained-release formulations of a composition of the invention may be made using conventional technology, in addition to the disclosure set forth elsewhere herein. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilitates the controlled-release of the active ingredient.

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

For oral administration, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more inert, non-toxic pharmaceutically excipients. Such excipients include, for example an inert diluent such as lactose; granulating and disintegrating agents such as cornstarch; binding agents such as starch; and lubricating agents such as magnesium stearate. The oral compositions of the invention in the form of tablets or capsules prepared by conventional means with pharmaceutically acceptable excipients such as binding agents; fillers; lubricants; disintegrates; or wetting agents.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. For oral administration, If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400).

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications.

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Kits of the Invention

The invention also includes a kit comprising a compound useful within the methods of the invention and an instructional material that describes, for instance, administering the compound to a subject as a prophylactic or therapeutic treatment or a non-treatment use as described elsewhere herein. In an embodiment, the kit further comprises a (preferably sterile) pharmaceutically acceptable carrier suitable for dissolving or suspending the therapeutic composition, comprising the compound useful within the methods of the invention, for instance, prior to administering the molecule to a subject. Optionally, the kit comprises an applicator for administering the compound.

Those skilled in the art will recognize or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

A kit may especially useful in cases of acute incidences, like traumatic brain injury, spinal cord injury, stroke, heart attack, acute glaucoma, near drowning, etc. in which the methods of the invention will further comprise or consist of invention also relates in part to a method of restoring heavy metal homeostasis in sick patient(s), comprising chronically administering to a sick patient a pharmaceutical composition consisting of from about 1 mg to less than about 200 mg of Posiphen or a pharmaceutically acceptable salt thereof together with one or more pharmaceutically acceptable excipients, on a once a day basis. By virtue of this method, treatment of a potential disease state such as a neurodegenerative disease, cardiovascular homeostasis, cancer, vital organ homeostasis, and the like.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

DETAILED DESCRIPTION OF PREFERRED EMBODIMENTS

The following examples further illustrate aspects of the present invention. However, they are in no way a limitation of the teachings or disclosure of the present invention as set forth herein.

The invention is now described with reference to the following Examples. These examples are provided for the purpose of illustration only, and the invention is not limited to these Examples, but rather encompasses all variations that are evident as a result of the teachings provided herein.

Example 1—Proof of Concept—Mechanism of Action

Based on the prior publication (Venti, et al. "The Integrated Role of Desferrioxamine and Phenserine Targeted to an Iron-Responsive Element in the APP-mRNA 5'-Untranslated Region", Ann. N.Y. Acad. Sci. 1035: pp. 34-48 (2004)), it was the understanding of those skilled in the art that Posiphen increased the binding of APP IRE mRNA to IRP1 and therefore reduced translation. However, when tested in a cell free recombinant system, Posiphen had no effect on binding of APP IRE to IRP1—the binding is identical. This was demonstrated in the following experiment.

RNA pulldown experiments were carried out by incubating 50 nM of biotinylated RNA oligos (GE Dharmacon, CO) and 5 µg of recombinant expressed IRP-1 (Mybiosource, CA) or alternatively using 100 µg of bacterial cell lysates expressing recombinant IRP-1. To obtain bacterial cell lysates expressing recombinant IRP-1, $E.\ coli$ BL21 pLysS was transformed with a pET29a vector encoding ACO1 gene optimized for bacterial expression. ACO1 was gene synthetized by Genscript and contains a His-tag at the N-terminal. Transformed cells were grown in LB media supplemented with 50 ug/ml Kanamycin and protein was expressed for 3 h at 30° C. by the addition of 0.5 mM IPTG at optical density of 0.6. Cells were then harvested for processing. Bacterial lysate was obtained by the addition of the lysis buffer (25 mM Tris pH 7.4, 0.5% Deoxycholate, 1% Triton X-100, 15 mM NaCl, 10 µM DTT, protease and RNAse inhibitors) and soluble fractions used in the binding experiments were then obtained by sonication and collecting the supernantant after centrifugation at 13,200 r.pm for 30 min. In case of the recombinant protein experiments, the incubation buffer consisted of 25 mM Tris pH 7.4, 0.5% Deoxycholate, 0.1 mg/ml BSA, 15 mM NaCl, 10 µM DTT and protease inhibitors. Recombinant protein/bacterial lysated were incubated with IRE RNAs, H-Ferritin (Biotin-GGGUUUCCUGCUUCAACAGUGCUUGGACGGAACCCGG) or APP (Biotin-GCG-GUGGCGGCGCGGGCAGAGCAAGGACGCGGCGGAU), for 1 h at 4 C following the addition of NeutrAvidin beads for an extra hour. After incubation, beads were washed multiple times with wash buffer (25 mM Tris pH 7.4, 0.5% Deoxycholate, 15 mM NaCl, and 10 µM DTT). After final wash samples were processed for SDS-PAGE and analyzed by Coomasie-staining or Western blot using anti-His antibodies. The results are shown in FIG. 1. In F1 lane 1 shows IRP1, lane 2 enriched IRP1. Lane 3 shows a band that migrates a little faster and it is IRP1 bound to biotin H-Ferritin mRNA; lane 4 also shows a faster migrating band which is IRP1 bound to biotin-APP. The results show pulldown of IRP1 using RNA biotinlylated RNAs (H-Ferr and APP) in combination with NeutrAvidin beads. As a positive control, Ni2+-NTA beads were used to pulldown IRP1. RNA was folded using the fast-cooling method. In sum, biotinylated H-ferritin IRE bound to recombinant IRP1 and biotinylated APP IRE also bound to IRP1.

Microscale thermophoresis (MST) binding experiments were done to assess binding in vitro between the different components. MST binding experiments were performed by incubating N-termini labeled protein (2 nM) with serial 2-fold dilutions of IRE RNAs, H-Ferritin (GGGGUUUCCUGCUUCAACAGUGCUUGGACGGAACC) or APP (GGUGGCGGCGCGGGCAGAGCAAGGACGCGGCG-GAU) for 10 min in incubation buffer (Tris pH 7.4, 0.5%, 15 mM NaCl and 0.1% Prionex). IPR-1 was N-termini labeled with RED-NHS amino reactive labeling kit (NanoTemper Technologies, Germany). For determination of Posiphen binding, reactions containing IPR1 (2 nM), IRP1/H-Ferritin (2, 250 nM), or IRP1/APP (2, 600 nM) were incubated for 10 min with 2-fold dilutions of Posiphen tartrate. After incubation, samples were centrifuged at 13,000 rpm for 2 minutes before being loaded into standard capillaries provided by the manufacturer. Fluorescence values from the binding reactions were determined using the Monolith NT.115 (Nano Temper Technologies). Kd values were using the NanoTemper Technologies software. Conditions were standardized.

Figure 2:
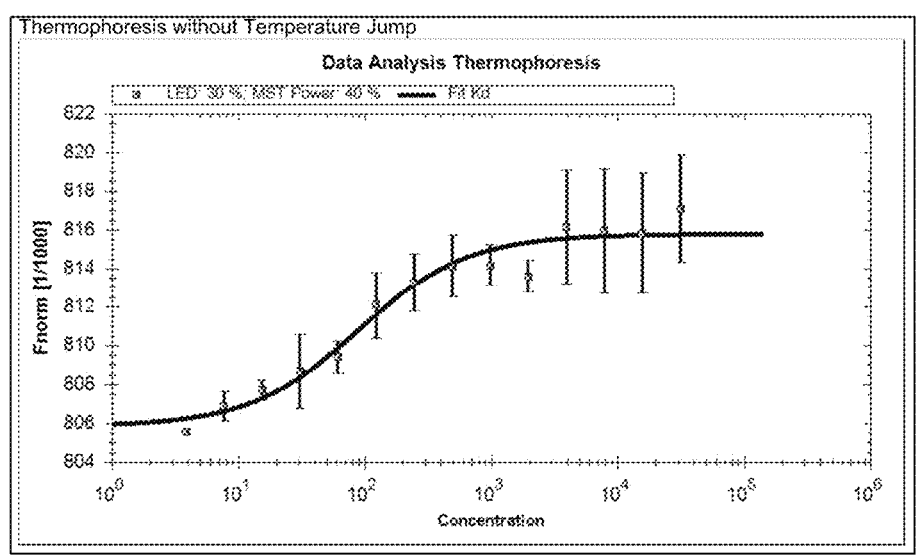
FIG. 2 is a graph showing the binding of the IRP1-H-Ferritin complex.
Figure 3:
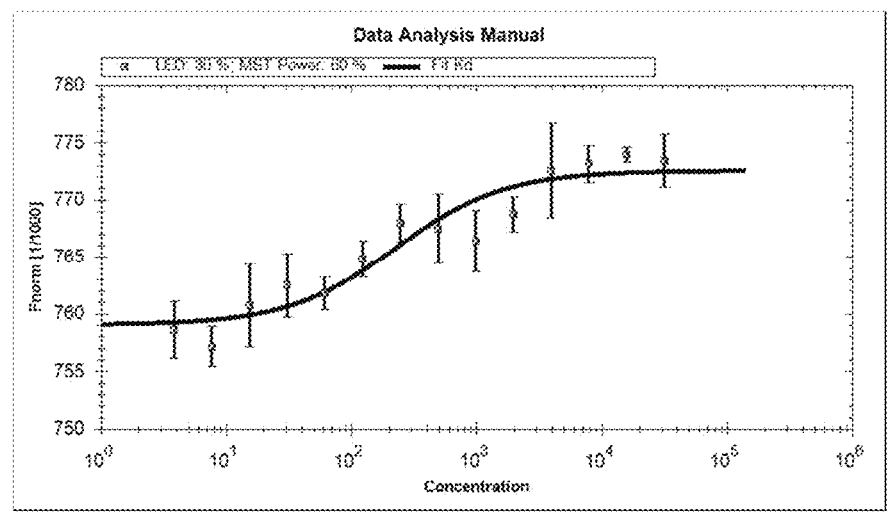
FIG. 3 is a graph showing the binding of the IRP1-APP complex.

The Kd for H-Ferritin was 88.5 nM. The Kd for APP was 225 nM. FIG. 2 shows the binding of the IRP1-H-Ferritin complexes. Conditions were standardized (fitting for Kd formula as follows: fitted parameter: fitted value; dissociation constant 88.5±15.8; Fluo. Conc. 2; Bound 815.80; Unbound 805.85; Amplitude 9.95; Kd Formula (law of mass action): f(c)=unbound+(bound-unbound)/2*(fluoConc+c+K). There was reliable binding curves showing binding of IRP1 to H-ferritin IRE RNA. The binding curve of APP IRE to IRP1-APP complexes is provided in FIG. 3. Conditions were standardized (fitting for Kd formula as follows: fitted parameter: fitted value; dissociation constant 225±47.8; Fluo. Conc. 2; Bound 772.58; Unbound 759.06; Amplitude 13.52; Kd Formula (law of mass action): f(c)=unbound+(bound-unbound)/2*(fluoConc+c+K). There was similar binding of IRP1 to H-Ferritin IRE RNA and APP IRE RNA. With respect to the MST assays of IRP1, H-Ferritin and Posiphen, there was no Kd, and the results indicated that there was no binding of Posiphen to the IRP1/H-Ferritan RNA complex. The binding for APP IRE/IRP1/Posiphen was Kd 3.2. These two graphs (FIGS. 1 and 2) correspond to the binding as shown on a Western blot in FIG. 1.

Figure 4:
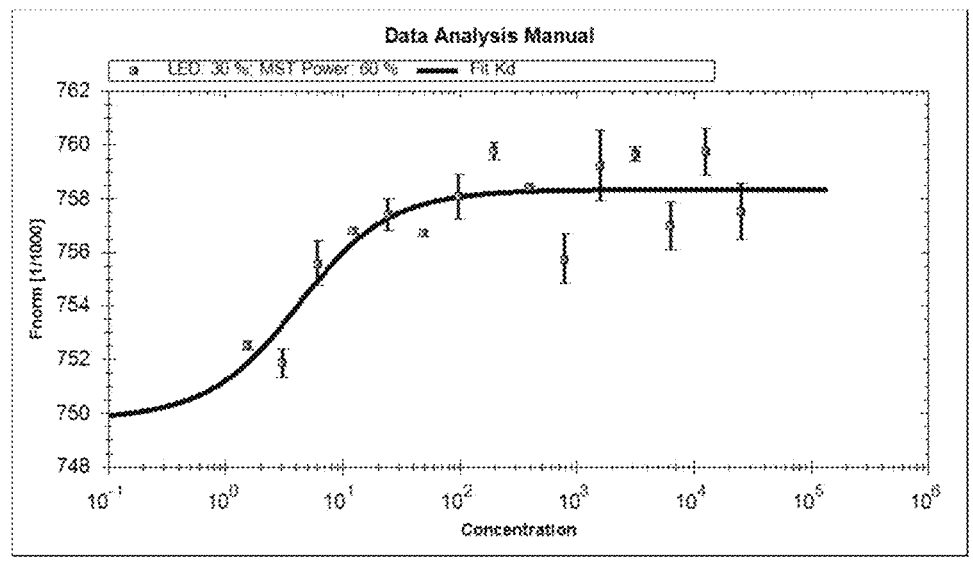
FIG. 4 is a graph showing the binding of IRP1/APP in the absence of Posiphen.
Figure 5:
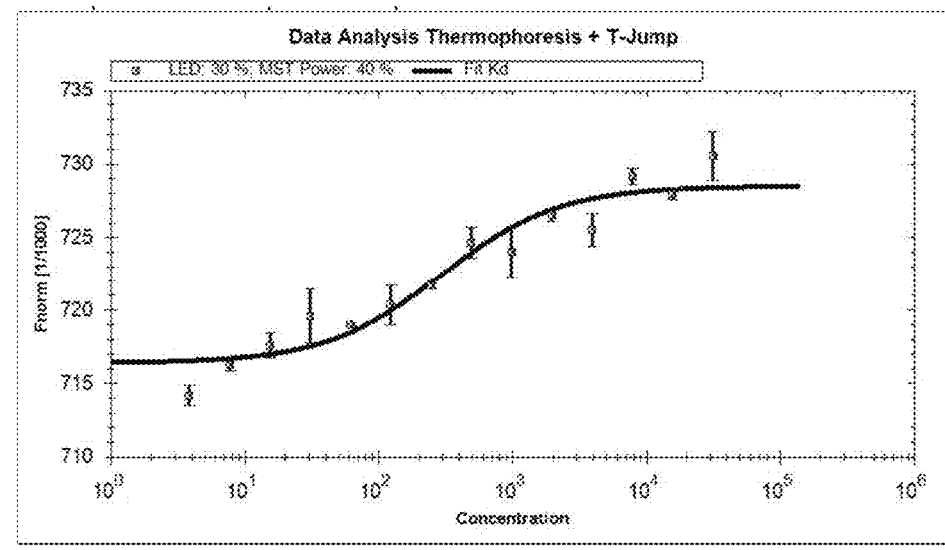
FIG. 5 is a graph showing the binding of IRP1/APP in the presence of Posiphen.

The binding curve of Posiphen to the APP IRE/IRP1 complex is provided in FIG. 4. Conditions were standardized (fitting for Kd formula as follows: fitted parameter: fitted value; dissociation constant 3.22±0.464; Fluo. Conc. 2; Bound 758.35; Unbound 749.76; Amplitude 8.59; Kd Formula (law of mass action): f(c)=unbound+(bound-unbound)/2*(fluoConc+c+K). The results indicated binding of Posiphen to the IRP1/APP RNA complex. However, the Kd for APP with Posiphen was Kd 295 nM, which indicates that Posiphen does not affect binding of APP IRE to IRP1 in a cell free system. The binding curve for APP IRE to IRP1 without Posiphen is shown in FIG. 4 and with Posiphen is shown in FIG. 5. FIGS. 4 and 5 together demonstrate that there is no difference in binding of IRP1/APP in the absence and presence of Posiphen. This is contrary to what we expected according to the publications discussed above (naming Jack Rogers as an author), which claim that Posiphen increases the binding of IRP1 to APP mRNA. It had been the understanding of the inventor that Posiphen increased the binding of APP IRE mRNA to IRP1 and therefore reduced translation. However, when tested in the cell free recombinant system, Posiphen had no effect on binding of APP IRE to IRP1—the binding is identical.

Figure 6:
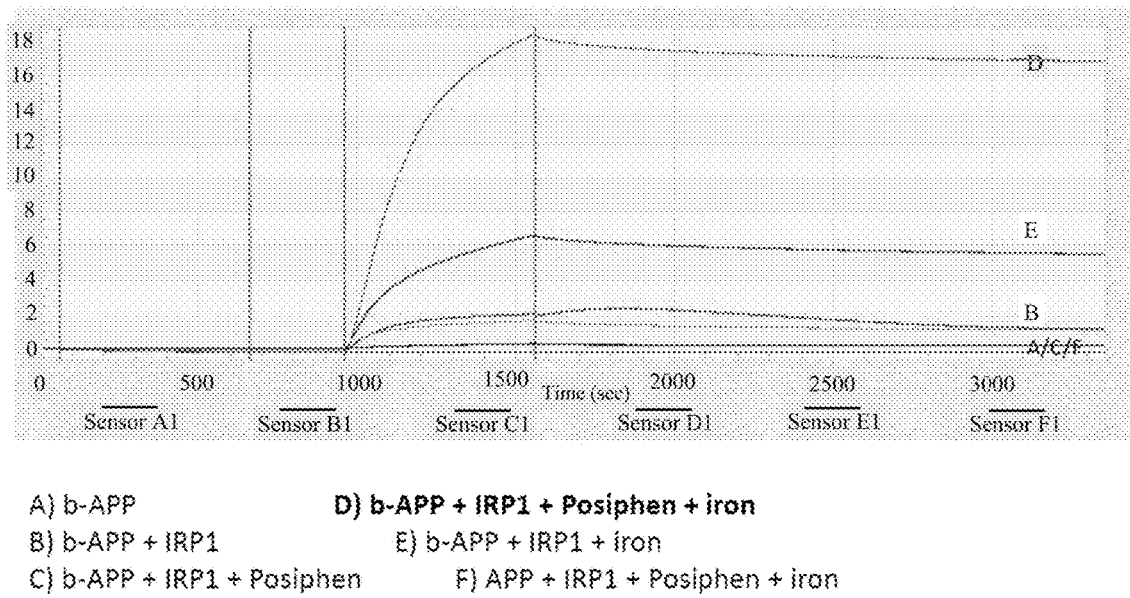
FIG. 6 is a graph showing APP IRE binding to IRP1 under different conditions.

Based on the above results, it was considered that a comparison of Posiphen binding in low iron versus high iron conditions was warranted. After trying binding in several conditions, we discovered that Posiphen in fact does increase binding of IRP1 to APP mRNA in the presence of iron. The results are provided in FIG. 6, which shows APP IRE binding to IRP1 under different conditions. As already shown biotin-APP IRE/IRP1 binding is not affected by Posiphen (B,C). The two controls biotin-APP and APP without biotin IRE/IRP1 also do not show any binding. However, with the addition of iron the binding of biotin is enhanced 4-fold and the addition of Posiphen increases binding 15 fold (compare curve D curve B). Therefore, we discovered that Posiphen only works in a state of iron dishomeostasis, which is present in dividing cell, sick cells and stressed cells. Thus, FIGS. 1 through 6 explain the mechanism of action of Posiphen.

Figure 7:
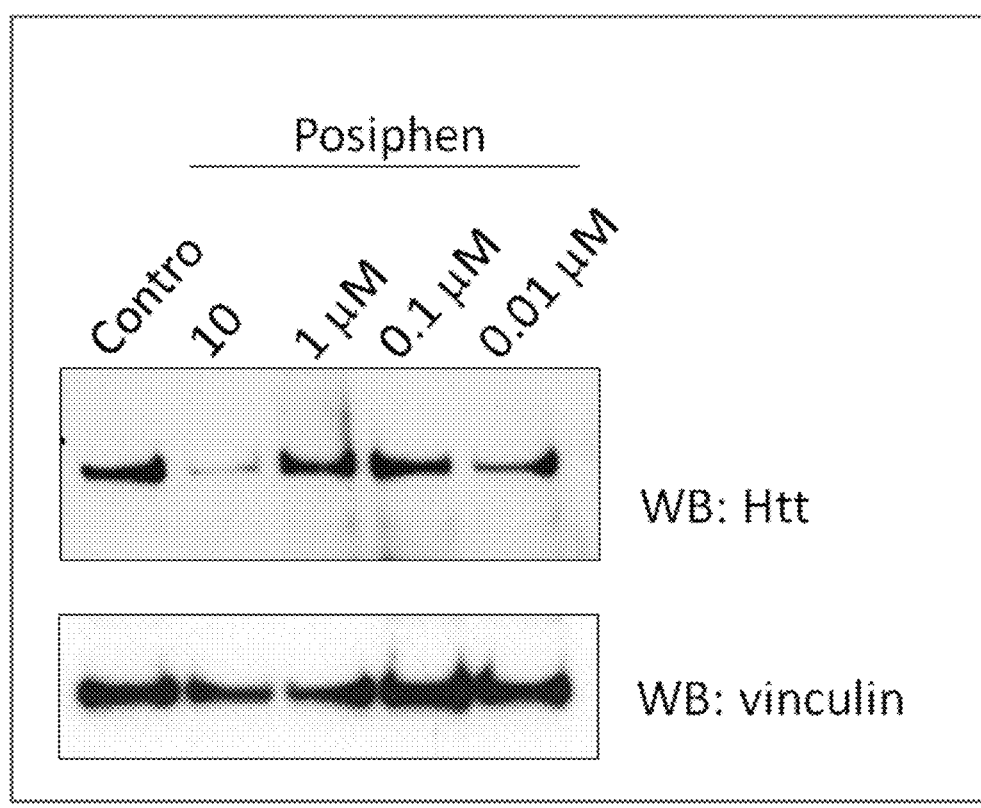
FIG. 7 is a Western Blot showing that Posiphen inhibits huntingtin's in a dose dependent fashion in healthy, dividing human fibroblast cells.
Figure 8:
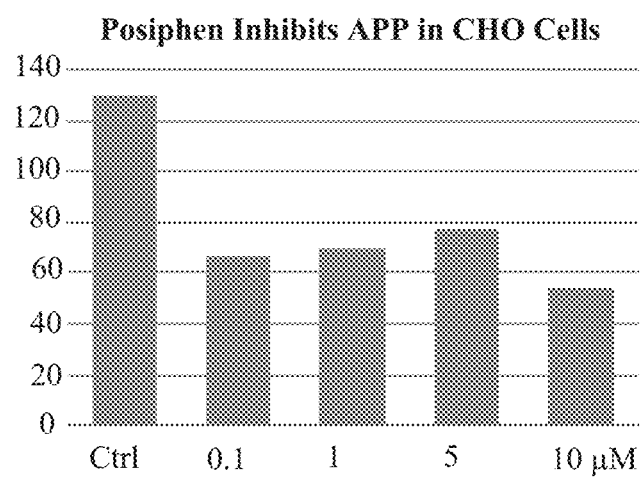
FIG. 8 is a graph showing inhibition of aSYN in healthy normal hamster ovary cells (CHO)

Example 2—Posiphen Inhibits Neurotoxic Aggregating Proteins in Dividing Cells In Example 2, Posiphen was administered to normal dividing cells (human fibroblasts) at concentrations of 10 µM, 1 µM, 0.1 µM and 0.01 µM, and a control (vinculin) was administered as well. Every single cell in the body, healthy or sick expresses some level of APP, tau, aSYN, htt, SOD1, prions, TDP43 and C9orf72. It is the level that makes them toxic. FIG. 7 is a Western blot assay showing that Posiphen inhibits htt in these cells. It shows that Posiphen inhibits huntingtin's in a dose dependent fashion in healthy, dividing human fibroblast cells. As an additional test, Posiphen was administered to Chinese hamster ovary cells (CHO). As shown in FIG. 8 (a bar diagram of a Western blot), Posiphen inhibits alpha-synuclein in a dose-dependent fashion in these healthy, normal hamster cells

Example 3—Stem Cells Respond to Posiphen; Differentiated Neurons do not

Figure 9:
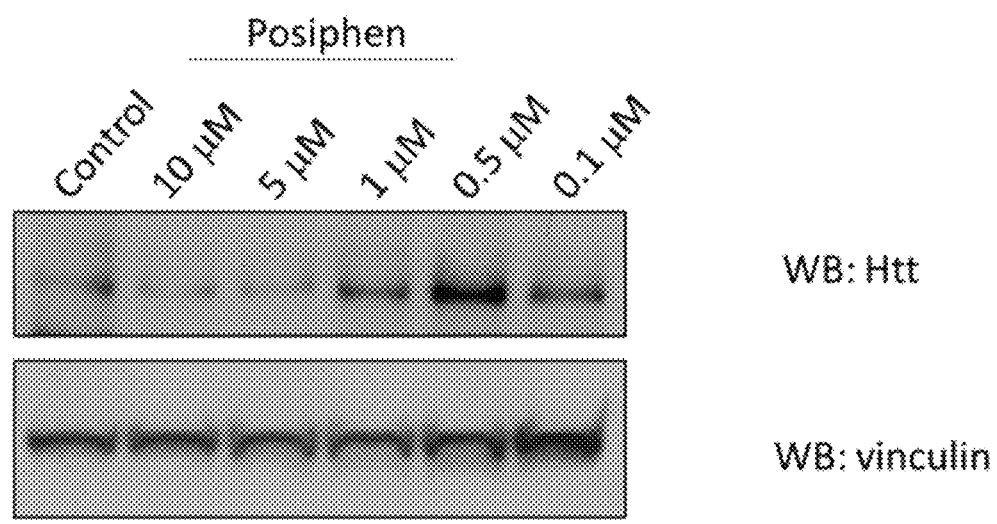
FIG. 9 is a Western Blot showing that in pluripotent stem cells Posiphen inhibits Htt in a dose dependent fashion.
Figure 10:
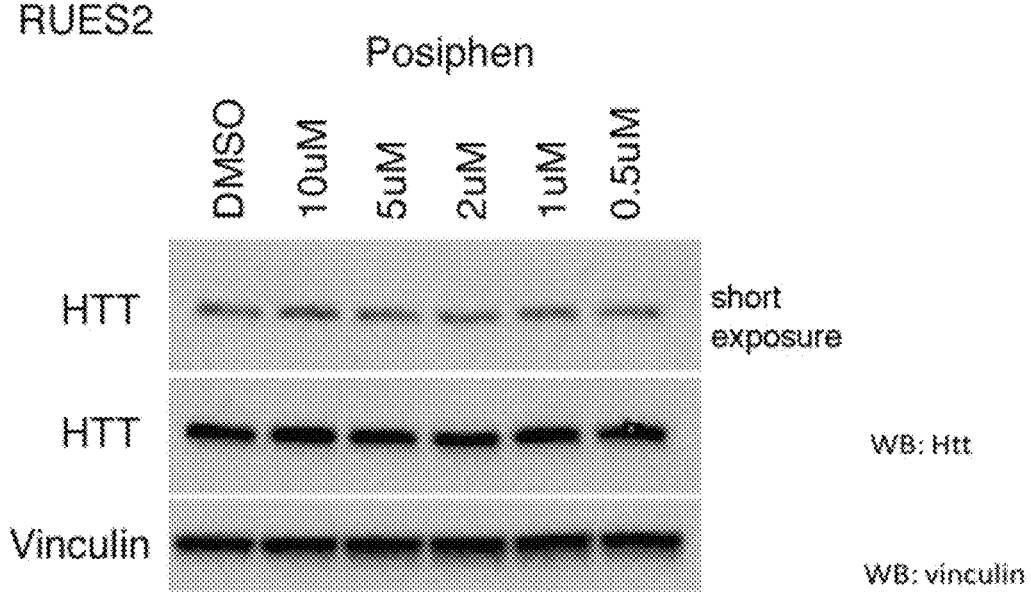
FIG. 10 is a Western Blot showing that once the pluripotent stem cells have been differentiated into neurons, Posiphen has no effect on Htt; aSYN.

In Example 3, the effect of Posiphen on pluripotent human embryonic stem cells (hESC) is shown. Pluripotent stem cells are undifferentiated cells that divide. Posiphen inhibits htt in such cells in a dose dependent fashion, as shown in FIG. 9 (Western blot). However, once these stem cells have been differentiated into neurons Posiphen has no effect on Htt, and even after prolonged exposure there is no change in the level of Htt, as shown in FIG. 10 (Western blot). Vinculin was used as a control in the experiments reported in FIGS. 9 and 10. It was concluded that Posiphen inhibits neurotoxic aggregating proteins in stem cells (dividing cells), but not in the differentiated nerve cells derived from them.

Example 4—Posiphen in Dividing and Cancerous Cells

Figure 11:
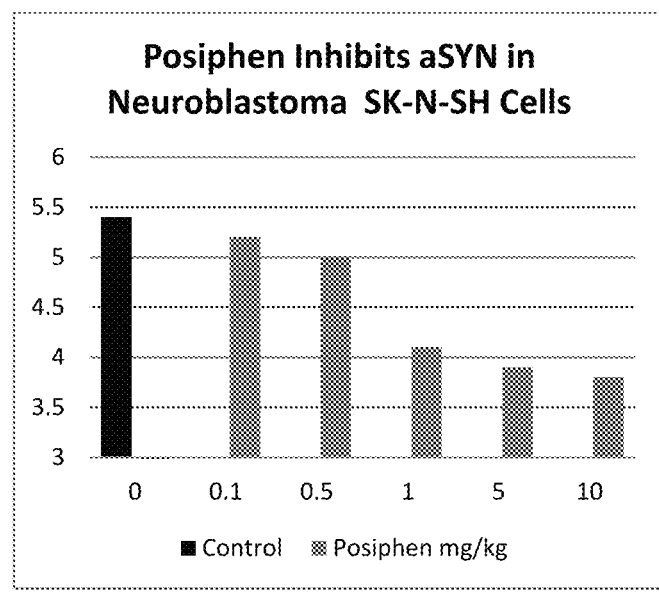
Figure 12:
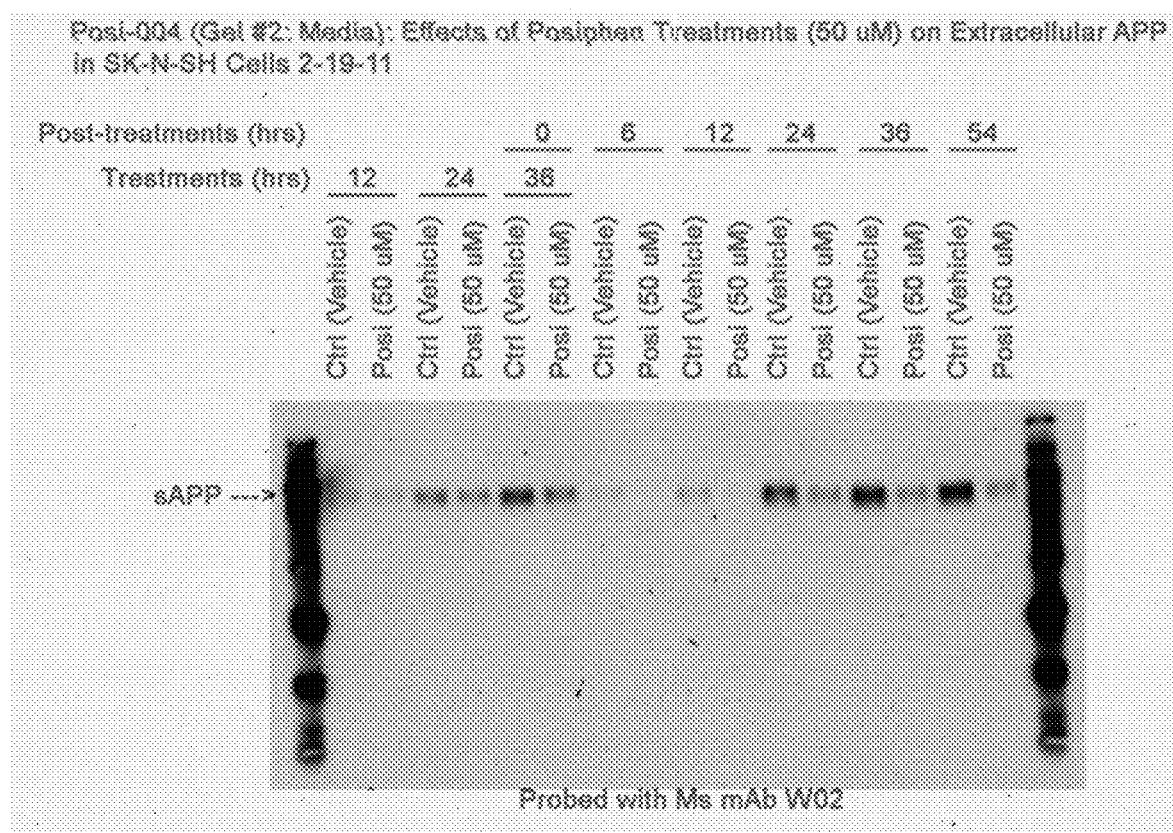
FIG. 12 is a graph showing the effect of Posiphen in neuroblastoma cells on APP.
Figure 13:
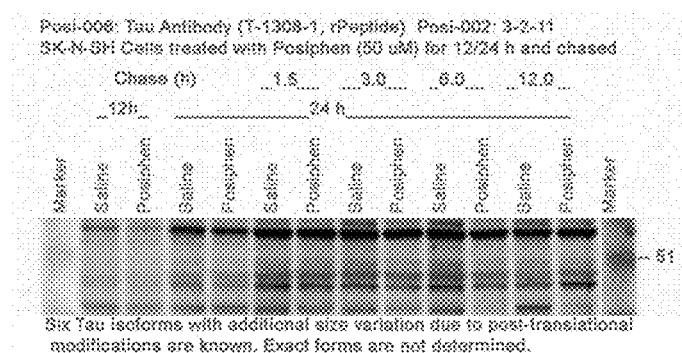
FIG. 13 is a graph showing the effect of Posiphen in neuroblastoma cells on tau.

In Example 4, Posiphen was tested in dividing and cancerous cells (SK-N-SH neuroblastoma cells) in order to demonstrate its effect on aSYN, APP and tau. As shown in FIG. 11, in SK-N-SH neuroblastoma cells Posiphen at levels from 0.1 to 10 uM inhibited aSYN in a dose dependent fashion. FIG. 12 is a Western blot showing the effects of Posiphen treatments (50 µM) on extracellular APP in SK-N-SH cells. Posiphen was administered for 12, 24 and 36 hours, and the bands were measured at 6, 12, 24, 36, and 54 hours after administration. Vehicle (control) was administered at the same times. As can be seen in FIG. 12, Posiphen inhibits APP in SK-N-SH neuroblastoma cells. FIG. 13 is a Western blot showing the activity of Posiphen against tau in SK-N-SH cells treated with Posiphen (50 µM) for 12/24 hours, versus control (saline). The last band of the Western blot was very affected, as well as the second to last band. From the results provided in Example 4, it was concluded that Posiphen inhibits neurotoxic aggregating proteins in cancerous cells. Thus, the effect of Posiphen in neuroblastoma cells is shown in FIG. 11 on aSYN, in FIG. 12 on APP, and in FIG. 13 on tau.

Figure 14:
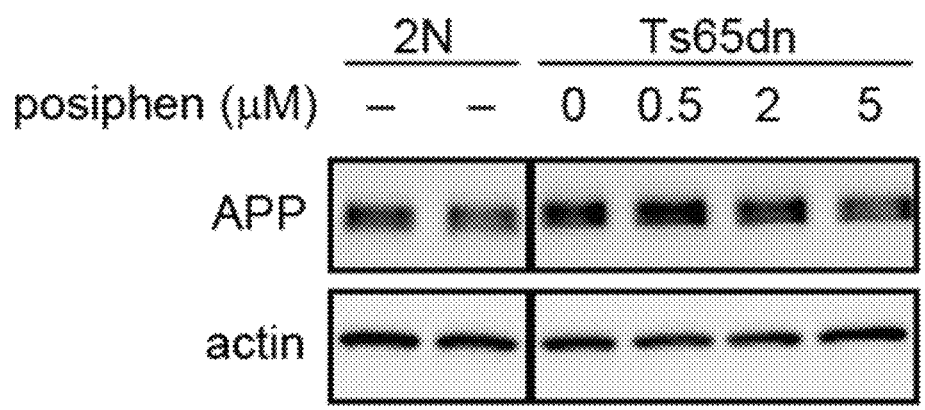
FIG. 14 is a Western Blot showing that Posiphen inhibits APP in 3N (triplication of chromosome 21) DS nerve cells, but does not inhibit APP in normal 2N (normal two chromosome 21) nerve cells.

Example 5—Posiphen Inhibits APP in Down Syndrome but not in Normal Fully Differentiated Normal Neurons Example 5, FIG. 14 shows that Posiphen inhibits APP in fully differentiated DS neurons, but not in normal fully differentiated neurons. Even though these 3N DS nerve cells are fully differentiated and non-dividing, Posiphen inhibits APP, while it does not do so in normal 2N nerve cells (FIG. 14). Due to the extra chromosome 21, these nerve cells are sick and therefore respond to Posiphen.

It was concluded that Posiphen inhibits neurotoxic aggregating proteins in abnormal DS fully differentiated nerve cells, but not in fully differentiated normal nerve cells.

Figure 15:
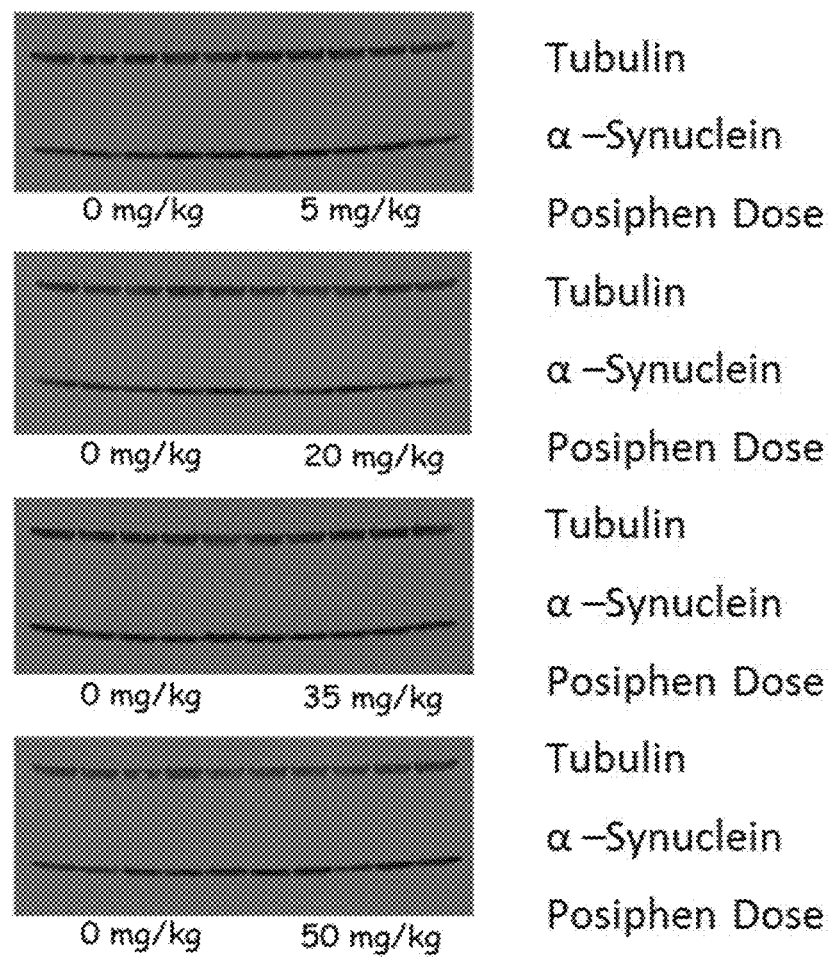
FIG. 15 is a Western Blot showing that Posiphen has no effect in the cortex of transgenic PD animals.

Example 6—Posiphen Inhibits Neurotoxic Aggregating Proteins in the Enteric Nerves of Transgenic PD Animals, but not in the Cortex of the Same Animals Example 6 shows the effect of Posiphen in aSYN transgenic PD animals. In Example 6, the effect of Posiphen on mice homozygous for the PAC-Tg(SNCAA53T) transgene was tested over the course of 21 weeks. These transgenic animals show constipation and aSYN aggregates in the gut, but do not show movement symptoms and have no aSYN aggregates in the brain. The results show that Posiphen lowers aSYN in enteric nerves of tg PD animals. As shown in the Western blot provided in FIG. 16, the band shows an inhibition of about 40% and that Posiphen has no effect in the cortex of these transgenic animals. —Posiphen did not act on the cortex of the same animals at doses of 5 mg/kg, 20 mg/kg, 35 mg/kg, and 50 mg/kg. In FIG. 15 (tubulin was used as a control), we show that Posiphen inhibits aSYN in the enteric nervous systems of these animals, because it acts in the gut. Since these animals have aSYN accumulation in the gut and not the brain, this makes sense. In the beginning, however, we believed according to Lahiri 2007 that we were supposed to see a decrease in the cortex and so we repeated the test multiple times, and no change in brain alpha-synuclein of tg aSYN PD mice was found (FIG. 15).

Example 7—Posiphen Inhibits Neurotoxic Aggregating Proteins in the Hippocampus of Transgenic APP/PS1 AD Animals, but not in the Cortex of the Same Animals In Example 7 looks at animals that show plaque and tangles in the hippocampus, but not in the rest of the brain. Posiphen was found to inhibit neurotoxic aggregating proteins in the hippocampus of transgenic APP/PS1 AD animals, but not in the cortex of the same animals. FIG. 17 is a Table showing that Posiphen inhibits APP and its fragments, like CTF-A, CTF-B, Abeta and tau, while there was no Posiphen effect in the cortex. These animals show plaques and tangles in the hippocampus and not in the cortex. Accordingly, we were able to show a decline in APP and its fragments as well as tau in the hippocampus. FIGS. 18*a-d* shows the effect of Posiphen on tangles (insoluble tau species) in the hippocampus of tau mice; a) on DA31 precipitable phospho-tau, b) on CP13 precipitable phospho-tau, c) on RZ3 precipitable phospho-tau and d) on PHF1 precipitable phospho-tau. We were able to further show a decrease in aggregated tau in the hippocampus.

It was concluded that Posiphen inhibits neurotoxic aggregating proteins in the hippocampus of transgenic AD animals APP and CTF-A and CTF-B (C-terminal fragments) but not in the cortex of the same animals

Figure 19:
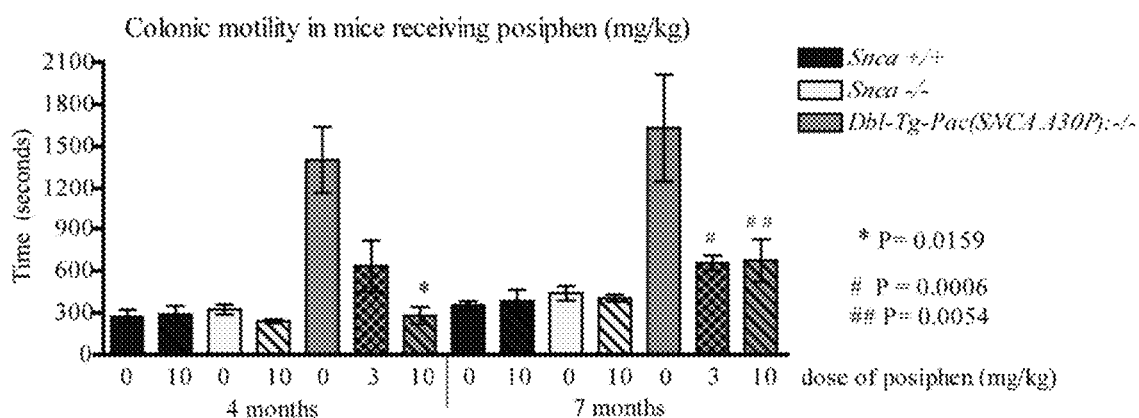
FIG. 19 a graph is showing the recovery from constipation in aSYN transgenic PD animals with the A30P mutation treated with Posiphen.
Figure 20:
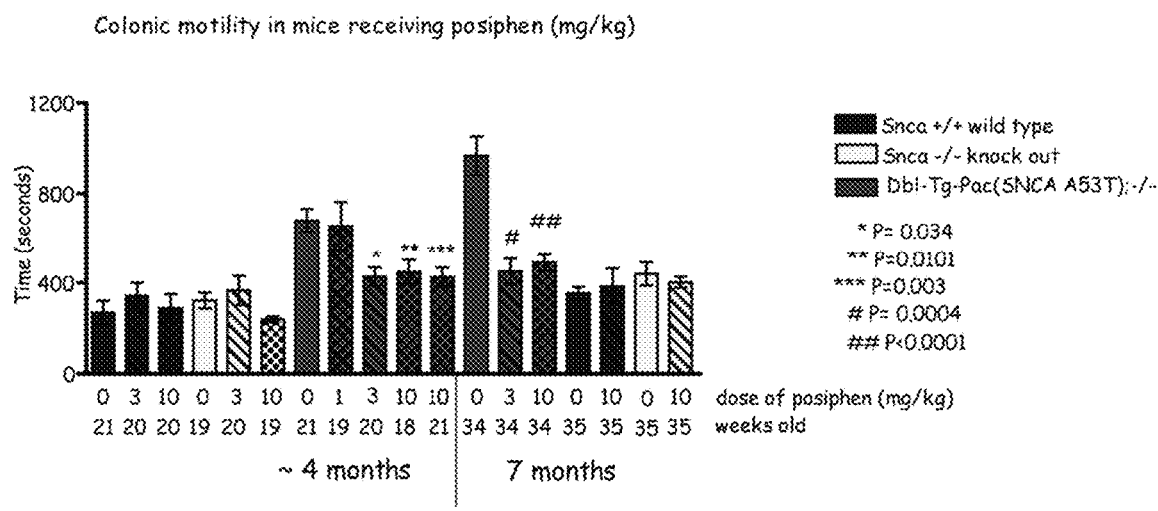
FIG. 20 is a graph showing the recovery from constipation in aSYN transgenic PD animals with the A53T mutation treated with Posiphen.

Example 8—Parkinson Mice: Posiphen Improves Gut Motility in Transgenic aSYN A30T and aSYN A53T In Example 8, Posiphen was shown to improve gut motility in transgenic aSYN A30T (F18) and A53T (F19) mice. These animals show constipation and when treated with Posiphen the constipation is relieved in a dose dependent fashion. Dbl-PAC-Tg(SNCAA30P); Snca$^{-/-}$ and control mice were treated with 0, 3 or 10 mg/kg IP daily from 6 to 28 weeks of age. FIG. 19 shows the recovery from constipation in the animals with the A30P mutation and FIG. 20 shows the recovery from constipation in the animals with the A53T mutation. The results show that colonic motility was 4 or 7 times slower in the saline mice. When treated with Posiphen, gut motility significantly increased and normalized to the gut motility of normal animals.

Figure 21:
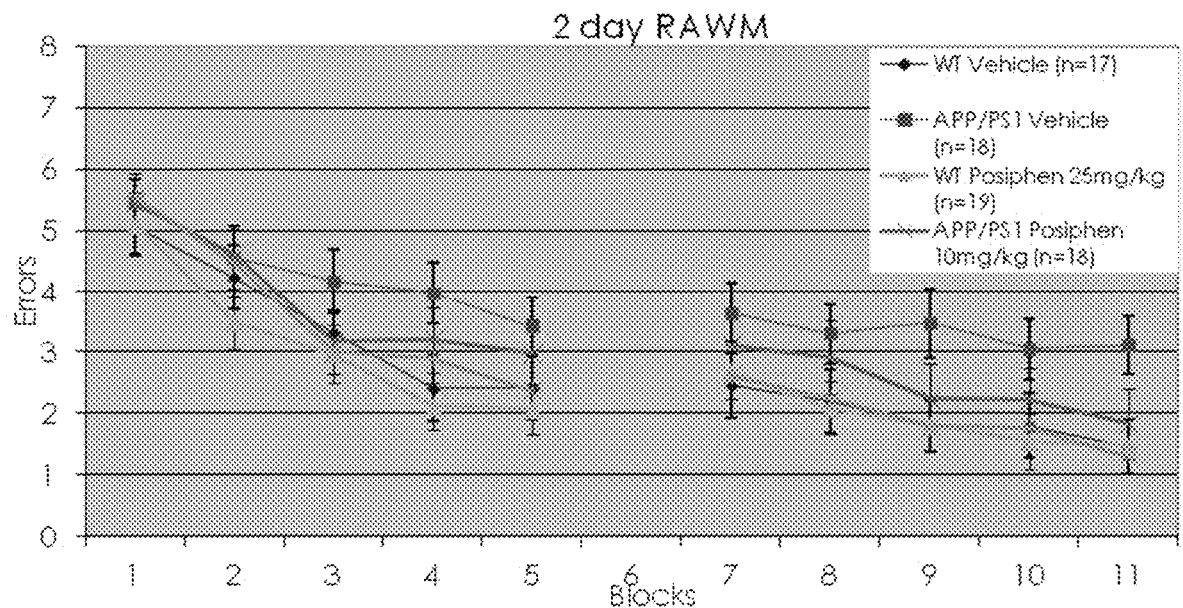
FIG. 21 is a graph showing the full recovery of memory and learning when Posiphen is administered in APP/PS1 transgenic AD animals.
Figure 22:
FIG. 22 is a graph showing an electrophysiological assay depicting long term potentiation effects of Posiphen in APP/PS1 transgenic AD animals.

Example 9—Posiphen Improves Spatial Memory and Long Term Potentiation in APPswe/PS1 Mice The memory and learning ability of these animals are compromised as measured by the mistakes they make to find the correct arm in the 7 arm water maze. In Example 9, Posiphen was shown to significantly improve (p=0.0033) the spatial memory of double transgenic (APPswe/PS1) mice in a radial water maze test. The results of testing these mice are reported in FIG. 21. After Posiphen administration the animals show full recovery of memory and learning. After euthanasia these same mice were tested for synaptic dysfunction as measured by long term potentiation (LTP) in hippocampal slices. Posiphen was shown to rescue synaptic dysfunction in hippocampal slices from APP/PS1 mice. See FIG. 22, which reports the results of electrophysiological assay testing on wild type mice and demonstrates that treatment with oral Posiphen reduced long-term potentiation in these mice and that administration of Posiphen fully recovers long term potentiation (e.g., increases the level of synaptic function up to the level seen in healthy mice).

Example 10—Acute Glaucoma Rats: Posiphen Protects Retinal Cells

Figure 23:
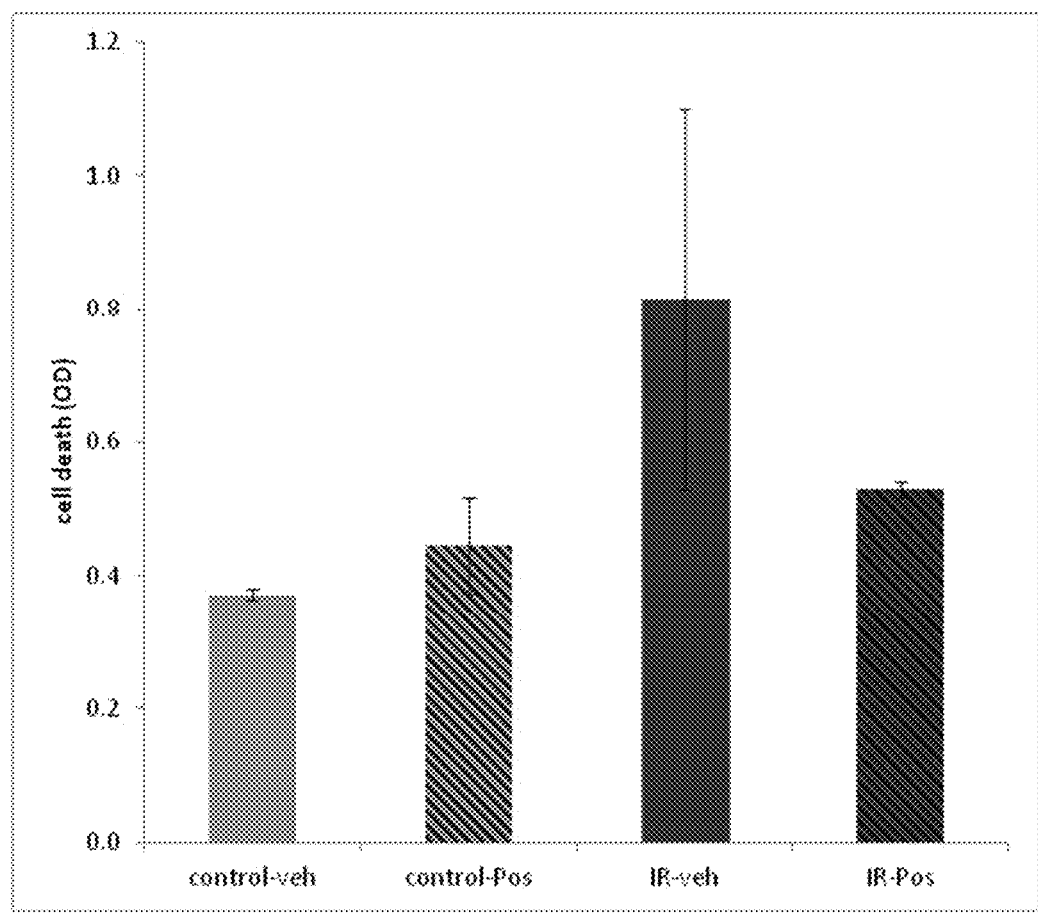
FIG. 23 is a graph showing the efficacy of Posiphen in preserving the retina and protecting the retinal cells in acute glaucoma.

When acute glaucoma is induced by increasing the pressure in an eye, the retina gets destroyed. In Example 10, acute glaucoma was induced in rats by increasing intraocular pressure by micro-injection of saline into the anterior chamber. This induces large amounts of apoptotic cell death in the retina. There are twice as many dead cells in high pressure retinas of rats treated with vehicle versus control untreated rats. Posiphen rescued 72% of the retinal neurons. The results are depicted in FIG. 23. Administration of Posiphen to those rats preserves the retina and protects the retinal cells from dying.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of maintaining heavy metal homeostasis in a healthy human or restoring heavy metal homeostasis in a sick human patient, comprising chronically administering a pharmaceutical composition comprising an active agent selected from the group consisting of Posiphen and pharmaceutically acceptable salts thereof, together with one or more pharmaceutically acceptable excipients in a therapeutically effective amount to maintain heavy metal homeostasis in the healthy human patient or restore heavy metal homeostasis in the sick human patient.

2. The method of claim 1, wherein the metal is iron.

3. The method of claim 1, wherein Posiphen is administered in an amount from about 1 mg to less than about 200 mg.

4. The method of claim 3, wherein Posiphen is administered orally on a once-a-day basis.

5. The method of claim 1, wherein Posiphen is administered in an amount from about 1 mg to about 30 mg, per day.

6. The method of claim 5, wherein Posiphen is administered orally.

7. The method of claim 1, wherein the chronic administration maintains heavy metal homeostasis in the healthy human.

8. The method of claim 1, wherein the chronic administration restores heavy metal homeostasis in the sick human patient.

9. The method of claim 1, wherein the administration of Posiphen prevents, stops, slows or delays the onset of a neurodegenerative disease or condition in a healthy human.

10. The method of claim 1, wherein the administration of Posiphen is to a sick human patient suffering from a neurodegenerative disease.

11. The method of claim 10, wherein the neurodegenerative disease is selected from the group consisting of Alzheimer's disease, Down Syndrome, alpha-synucleopathies, Parkinson's disease, Huntington's disease, Prion's disease, Amyloid Lateral Sclerosis, Multiple Sclerosis, Tauopathies and other chronic and acute neurodegenerative disorders.

12. The method of claim 1, wherein the administration of Posiphen prevents, stops, slows or delays the onset of cancer in the healthy human.

13. The method of claim 1, wherein the administration of Posiphen prevents, stops, slows or delays the course of cancer in a sick human patient suffering from cancer.

14. The method of claim 1, wherein the administration of Posiphen prevents, stops, slows or delays the onset of cardiovascular disease in the healthy human.

15. The method of claim 1, wherein the administration of Posiphen prevents, stops, slows or delays the course of cardiovascular disease in the sick human patient.

16. The method of claim 1, wherein the administration of Posiphen maintains homeostasis in vital organs in the healthy human.

17. The method of any of claim 1, wherein the administration Posiphen restores homeostasis in vital organs in the sick human patient.

18. The method of claim 17, wherein the vital organ is selected from brain, heart, lung, liver, a kidney.

19. The method of claim 1, wherein the chronic administration is to a patient who has suffered an acute injury/incidence such that there is stasis or amelioration of symptoms or effects of the acute injury/incidence.

20. The method of claim 1, wherein Posiphen is administered via a route selected from the group consisting of oral, parenteral, sublingual, a suppository, nasal, topical, transdermal, and an implant under the skin.

* * * * *